(12) United States Patent
Buerstedde et al.

(10) Patent No.: US 8,742,081 B2
(45) Date of Patent: Jun. 3, 2014

(54) FLUORESCENT GFP VARIANT DISPLAYING HIGHLY INCREASED FLUORESCENCE INTENSITY WITHOUT A SPECTRAL SHIFT

(75) Inventors: Jean-Marie Buerstedde, München (DE); Hiroshi Arakawa, München (DE)

(73) Assignee: Helmholtz Zentrum Munchen Deutsches Forschungszentrum fur Gesundheit und Umwelt (GmbH) (DE)

( * ) Notice: Subject to any disclaimer, the term of this patent is extended or adjusted under 35 U.S.C. 154(b) by 210 days.

(21) Appl. No.: 12/671,495

(22) PCT Filed: Aug. 1, 2008

(86) PCT No.: PCT/EP2008/006372
§ 371 (c)(1),
(2), (4) Date: Nov. 29, 2010

(87) PCT Pub. No.: WO2009/015904
PCT Pub. Date: Feb. 5, 2009

(65) Prior Publication Data
US 2011/0059443 A1    Mar. 10, 2011

(30) Foreign Application Priority Data
Aug. 1, 2007   (EP) .................................. 07015111

(51) Int. Cl.
*C07H 21/04*    (2006.01)
(52) U.S. Cl.
USPC ........................................ 536/23.1; 536/23.4
(58) Field of Classification Search
None
See application file for complete search history.

(56) References Cited

U.S. PATENT DOCUMENTS 5,777,079 A * 7/1998 Tsien et al. ................... 530/350

OTHER PUBLICATIONS

Heim, R., Green Fluorescent Protein Forms for Energy Transfer, Methods in Enzymology, 1999, 302:408-423.
Heim, R., Engineering Green Fluorescent Protein for Improved Brightness, Longer Wavelengths and Fluorescence Resonance Energy Transfer, Current Biology, 1996, 6(2):178-182.

* cited by examiner

*Primary Examiner* — Michael Burkhart
(74) *Attorney, Agent, or Firm* — Pillsbury Winthrop Shaw Pittman LLP

(57) ABSTRACT

The present invention relates to a nucleic acid molecule encoding a polypeptide having a fluorescence emission activity with a maximum emission at 505 to 515 nm, wherein said nucleic acid molecule is selected from the group consisting of (a) a nucleic acid molecule encoding a polypeptide having the amino acid sequence of SEQ ID NO: 2; (b) a nucleic acid molecule having the DNA sequence of SEQ ID NO: 1; (c) a nucleic acid molecule hybridizing under stringent conditions to the complementary strand of (i.) a nucleic acid molecule of (a), wherein said nucleic acid molecule of (c) encodes a polypeptide having at the position corresponding to position 146 of SEQ NO:2 a phenylalanine and at the position corresponding to position 203 of SEQ NO:2 a threonine; or (ii) a nucleic acid molecule of (b), wherein said nucleic acid molecule of (c) has at the positions corresponding to positions 438 to 440 of SEQ ID NO: 1 a nucleotide triplet selected from the group consisting of TTT and TTC; and at the positions corresponding to positions 609 to 611 of SEQ ID NO: 1 a nucleotide triplet selected from the group consisting of ACT, ACC, ACA, ACG; wherein the polypeptide encoded by the nucleic acid molecule of (c) has a fluorescence enhanced by at least the factor of 2.5 as compared to the polypeptide having the amino acid sequence of SEQ ID NO: 10; or (d) a nucleic acid molecule degenerate with respect to the nucleic acid molecule of (b). The present invention furthermore relates to a polypeptide encoded by the nucleic acid molecule of the invention, a vector and a host cell comprising the nucleic acid molecule of the invention, a method of producing said polypeptide, a fusion protein comprising the polypeptide of the invention and methods of detecting the presence and/or localization of a protein of interest and methods of detecting the activity of a promoter.

11 Claims, 8 Drawing Sheets

FIG. 2B

AIDR1 IgL eGFP1    sort III

Figure 1A:
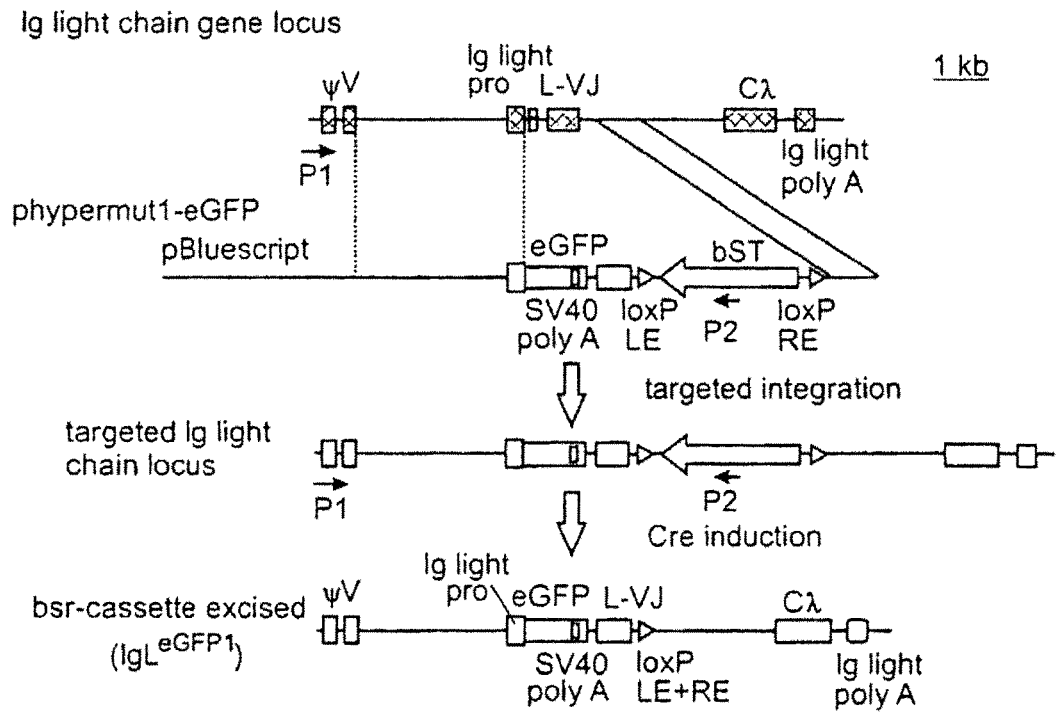

```
     1  1a 2                                    10                            20
     M  V  S  K  G  E  E  L  F  T  G  V  V  P  I  L  V  E  L  D  G  D  Y  N  G  H  K  F  S  V
    atg gtg agc aag ggg gag gag ctg ttc acc ggg gtg gtc ccc atc ctg gtc gag ctg gac ggc gac gta aac ggc cac aag ttc agc gtg     90

30                             40                                  50
     S  G  E  G  E  G  D  A  T  Y  G  K  L  T  L  K  F  I  C  T  T  G  K  L  P  V  P  W  P  T
    tcc ggc gag ggc gag ggc gat gcc acc tac ggc aag ctg acc ctg aag ttc atc tgc acc acc ggc aag ctg ccc gtg ccc tgg ccc acc    180
                                                                                                                        t
                                                                                                                        S
    60       65 66 67              70                                  80
     L  V  T  T  L  T  Y  G  V  D  C  F  S  R  Y  P  D  H  M  K  D  H  D  F  F  K  S  A  M  P
    ctc gtg acc acc ctg acc tac ggc gtg cag tgc ttc agc cgc tac ccc gac cac atg aag gac cac gac ttc ttc aag tcc gcc atg ccc    270
                             S t                                       R              E
                                                                       g              g63
    90                             100                                 110
     E  G  Y  V  Q  E  R  T  I  F  F  K  D  D  G  N  Y  K  T  R  A  E  V  K  F  E  G  D  T  L
    gaa ggc tac gtc cag gag cgc acc atc ttc ttc aag gac gac ggc aac tac aag acc cgc gcc gag gtg aag ttc gag ggc gac acc ctg    360
                                                           D C4
    120                            130                                 140
     V  N  R  I  E  L  K  G  I  D  F  K  E  D  G  N  I  L  G  H  K  L  E  Y  N  Y  N  S  H  N
    gtg aac cgc atc gag ctg aag ggc atc gac ttc aag gag gac ggc aac atc ctg ggg cac aag ctg gag tac aac tac aac agc cac aac    450
                                     D                                      g1  D  C   E   t6
                                     C12                                        a24 a6
    150                            160                                 170
     V  Y  I  M  A  D  K  Q  K  N  G  I  K  V  N  F  K  I  R  H  N  I  E  D  G  S  V  Q  L  A
    gtc tat atc atg gcc gac aag cag aag aac ggc atc aag gtg aac ttc aag atc cgc cac aac atc gag gac ggc agc gtg cag ctc gcc    540
                                                           A                c4
    180                            190                                 200
     D  H  Y  Q  Q  N  T  P  I  G  D  G  P  V  L  L  P  D  N  H  Y  L  S  T  Q  S  A  L  S  K
    gac cac tac cag cag aac acc ccc atc ggc gac ggc ccc gtg ctg ctg ccc gac aac cac tac ctg agc acc cag tcc gcc ctg agc aaa    630
                   E                             v  a3                      t9                                     a20    t2
                   g20                           g2                         t5
    210                            220                                 230
     D  P  N  E  K  R  D  H  M  V  L  L  E  F  V  T  A  A  G  I  T  L  G  M  D  E  L  Y  K  S
    gac ccc aac gag aag cgc gat cac atg gtc ctg ctg gag ttc gtg acc gcc gcc ggg atc act ctc ggc atg gac gag ctg tac aag tcc    720
                                        D  L                                                      L
                                        C  C5                                                     a3
    240
    tag 723
```

FLUORESCENT GFP VARIANT DISPLAYING HIGHLY INCREASED FLUORESCENCE INTENSITY WITHOUT A SPECTRAL SHIFT

RELATED APPLICATIONS:

This application is the National Phase of International Application PCT/EP2008/006372 filed Aug. 1, 2008 which designated the U.S. and that International Application was published under PCT Article 21(2) in English, and claims priority to European Application Serial No. 07015111.3, filed Aug. 1, 2007, all of which applications are incorporated herein by reference in their entirety.

The present invention relates to a nucleic acid molecule encoding a polypeptide having a fluorescence emission activity with a maximum emission at 505 to 515 nm, wherein said nucleic acid molecule is selected from the group consisting of (a) a nucleic acid molecule encoding a polypeptide having the amino acid sequence of SEQ ID NO: 2; (b) a nucleic acid molecule having the DNA sequence of SEQ ID NO: 1; (c) a nucleic acid molecule hybridizing under stringent conditions to the complementary strand of (i.) a nucleic acid molecule of (a), wherein said nucleic acid molecule of (c) encodes a polypeptide having at the position corresponding to position 146 of SEQ NO:2 a phenylalanine and at the position corresponding to position 203 of SEQ NO:2 a threonine; or (ii) a nucleic acid molecule of (b), wherein said nucleic acid molecule of (c) has at the positions corresponding to positions 438 to 440 of SEQ ID NO: 1 a nucleotide triplet selected from the group consisting of TTT and TTC; and at the positions corresponding to positions 609 to 611 of SEQ ID NO: 1 a nucleotide triplet selected from the group consisting of ACT, ACC, ACA, ACG; wherein the polypeptide encoded by the nucleic acid molecule of (c) has a fluorescence enhanced by at least the factor of 2.5 as compared to the polypeptide having the amino acid sequence of SEQ ID NO: 10; or (d) a nucleic acid molecule degenerate with respect to the nucleic acid molecule of (b). The present invention furthermore relates to a polypeptide encoded by the nucleic acid molecule of the invention, a vector and a host cell comprising the nucleic acid molecule of the invention, a method of producing said polypeptide, a fusion protein comprising the polypeptide of the invention and methods of detecting the presence and/or localization of a protein of interest as well as methods of detecting the activity of a promoter.

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The usefulness of Aequorea Victoria Green Fluorescent Protein (GFP) was first shown in 1994 (Chalfie et al., 1994). The protein sequence derived from the cDNA nucleotide sequence (Prasher et al., 1992) contains 238 amino acid residues and led to the determination of the chromophore structure, consisting of the residues Ser65, Tyr66 and Gly67. Nucleotide sequences derived from Aequorea indicate that at least five variants of GFP exist. Lately, also homologous fluorescent proteins form distantly related sea creatures have been discovered. The fluorescent properties of GFP make it an especially useful tool in living cells and tissue. Substantial trials were carried out over the years to optimize the properties of the wild-type GFP. The earliest modifications of wild-type GFP were directed at improving the ability to express the protein in mammalian cell systems at 37° C. after it was previously shown to express in prokaryotic cells. Other improvements included simplification of the extinction spectrum, increasing the fluorescence intensity of the protein by increasing the extinction coefficient as well as increasing the speed and efficiency of folding, making different colours or spectral mutants, reducing the sensitivity to pH and halides and most recently reducing the tendency of the protein to dimerize.

Starting from wild-type GFP, seven classes of GFP-derived proteins were established based on the distinctive component of their chromophores which summarize spectral mutants of the protein obtained by introducing amino acid mutations (Tsien, 1998; Zacharias and Tsien, 2006). Green fluorescent proteins belong to class 2 having a phenolate anion. The prototype of this class incorporates the mutation S65T which results in a high increase in the amplitude and a red shift of the excitation wavelength from 475 to 488 nm as well as in a suppression of the excitation maximum at 395 nm (Delagrave et al., 1995, Heim et al., 1995; Cheng et al., 1996). The proteins of this class generally have an emission maximum in the range of 507 to 511 nm which resembles that of wild-type GFP. The formation of the mature chromophore in this mutant is about four times faster than in the wild-type and folding was comparably efficient at temperatures lower than 37° C.

The following properties of GFP are most often targeted by experimentally generated mutations: the folding of GFP in the cell which naturally occurs quite slowly. It should be enhanced. Furthermore, the brightness or fluorescent intensity of the protein should be enhanced in order to enable for more sensitive detection of weak signals and/or detection in mammalian cells with a naturally higher autofluorescence-background.

Furthermore, some trials aimed at disrupting the dimerization domain of GFP. GFP naturally occurs as a dimer which can lead to unwanted protein aggregation and can render the proteins connected to these proteins to loss-of function proteins, so that the results obtained are not reliable.

Despite substantial trials to improve the fluorescence intensity of GFP, the results achieved so far are mostly not limited to such enhancement. Most mutations or combinations of mutations applied resulted in the alteration of more than one properties of GFP, most often also in a shift in the absorption and/or emission spectra.

Blue and cyan variants derived from GFP have one or more mutations in the chromophore, i.e. at positions 64, 65 and 66, naturally occupied by Phe64, Ser65 and Tyr66 in wild-type GFP. Other mutations, such as V163A, are supposed to improve the folding properties and/or thermostability of the protein (Siemering et al., 1996) although, according to the U.S. Pat. No. 5,968,738, the effect of the addition of this mutation to GFP variants, e.g. those identified by Heim et al. (1995), is not a priori predictable. Anderson at al. (1996) report that the two mutations S65T and V163 have a synergistic effect and show a more increased fluorescence intensity than would have been expected from the addition of the single mutations. The V163A codon substitution is also included in the GFP variants Cycle3 (Patterson et al., 1997)), T-Sapphire (Kanayama et al., 2006), Venus (Zapata-Hommer and Griesbeck, 2003; Nagai et al., 2002; Rekas et al, 2002), ECFP (Cubitt et al, 1999) and W1C (Cubitt et al, 1999). It has been proposed that the V163A substitution facilitates the correct folding and maturation of GFP (Zacharias and Tsien, 2006). Mutated GFP comprising an S202F exchange in combination with a T203l exchange is not brighter than wild-type GFP. In addition, both mutations are known to cause the loss of excitation in the 475 region with preservation of 395 nm excitation rendering the resulting GFP variant less suitable for use in biological applications. Also, the mutation Y145F was shown to be capable of increasing the fluorescence intensity in combination with other mutations and is shared by the GFP variants Sapphire (Kanayama et al., 2006), p4-3 (Cubitt et al., 1999) and EBFP (Patterson et al., 1997; Cubitt et al., 1999), whereas mutations such as Q80R or H231L were shown to be phenotypically neutral (reviewed in Zacharias and Tsien, 2006).

The currently available GFP variants, e.g. eGFP (Cormack et al., 1996), have limited use due to the lower fluorescence intensity as compared to the available spectrally shifted YFP variants. The literature terminology is confusing as GFP variants referred to as being brighter are actually the spectrally shifted YFP variants more often than not. Brighter fluorescent probes of all shades but especially in the range of GFPs are needed by the entire scientific and medical research communities.

In summary, whereas the prior art has achieved certain improvements concerning the stability and the fluorescence intensity of GFP and proteins derived therefrom, there are still major drawbacks arising from a comparably low fluorescence intensity when GFP is applied in mammalian cells and also in comparison to other fluorescent proteins having a higher fluorescence intensity. The technical problem to be solved was therefore to provide GFP variants with improved fluorescence intensity but retaining essentially the same absorption and/or emission spectrum as compared to wild-type GFP.

The solution to said technical problem is achieved by providing the embodiments characterized in the claims.

The present invention relates to a nucleic acid molecule encoding a polypeptide having a fluorescence emission activity with a maximum emission at 505 to 515 nm, wherein said nucleic acid molecule is selected from the group consisting of (a) a nucleic acid molecule encoding a polypeptide having the amino acid sequence of SEQ ID NO: 2;
(b) a nucleic acid molecule having the DNA sequence of SEQ ID NO: 1;
(c) a nucleic acid molecule hybridizing under stringent conditions to the complementary strand of
   i. a nucleic acid molecule of (a), wherein said nucleic acid molecule of (c) encodes a polypeptide having at the position corresponding to position 146 of SEQ NO:2 a phenylalanine and at the position corresponding to position 203 of SEQ NO:2 a threonine; or
   ii. a nucleic acid molecule of (b), wherein said nucleic acid molecule of (c) has at the positions corresponding to positions 438 to 440 of SEQ ID NO: 1 a nucleotide triplet selected from the group consisting of TTT and TTC; and at the positions corresponding to positions 609 to 611 of SEQ ID NO: 1 a nucleotide triplet selected from the group consisting of ACT, ACC, ACA, ACG; wherein the polypeptide encoded by the nucleic acid molecule of (c) has a fluorescence enhanced by at least the factor of 2.5 as compared to the polypeptide having the amino acid sequence of SEQ ID NO: 10;
or
(d) a nucleic acid molecule degenerate with respect to the nucleic acid molecule of (b).

The term "nucleic acid molecule" as used interchangeably with the term "polynucleotide", in accordance with the present invention, includes DNA, such as cDNA or genomic DNA, and RNA. Further included are nucleic acid mimicking molecules known in the art such as synthetic or semi-synthetic derivatives of DNA or RNA and mixed polymers. Such nucleic acid mimicking molecules or nucleic acid derivatives according to the invention include phosphorothioate nucleic acid, phosphoramidate nucleic acid, 2'-O-methoxyethyl ribonucleic acid, morpholino nucleic acid, hexitol nucleic acid (HNA) and locked nucleic acid (LNA) (see Braasch and Corey, Chem Biol 2001, 8: 1). LNA is an RNA derivative in which the ribose ring is constrained by a methylene linkage between the 2'-oxygen and the 4'-carbon. They may contain additional non-natural or derivative nucleotide bases, as will be readily appreciated by those skilled in the art. Such nucleic acid derivatives are also useful in connection with the GFP variants of the present invention when it comes to engineering reporters by insertion of these nucleic acid (NA) derivatives into the sequence encoding the GFP variant of the invention.

The term "polypeptide" as used herein interchangeably with the term "protein" describes linear molecular chains of amino acids, including single chain proteins or their fragments, containing more than 30 amino acids. Polypeptides may further form oligomers consisting of at least two identical or different molecules. The corresponding higher order structures of such multimers are, correspondingly, termed homo- or heterodimers, homo- or heterotrimers etc. Furthermore, peptidomimetics of such proteins/polypeptides where amino acid(s) and/or peptide bond(s) have been replaced by functional analogues are also encompassed by the invention. Such functional analogues include all known amino acids other than the 20 gene-encoded amino acids, such as selenocysteine. The terms "polypeptide" and "protein" also refer to naturally modified polypeptides/proteins where the modification is effected e.g. by glycosylation, acetylation, phosphorylation and similar modifications which are well known in the art.

Fluorescence is the result of a three-stage process that occurs in certain molecules called fluorophores or fluorescent dyes, inter alia fluorescent proteins. This is conveniently illustrated by an electronic-state diagram (Jablonski diagram) easily retrievable by the person skilled in the art. A fluorescent probe is a fluorophore designed to localize within a specific region of a biological specimen or to respond to a specific stimulus.

In stage 1, a photon of energy $h\nu_{Ex}$ is supplied by an external source such as an incandescent lamp or a laser and absorbed by the fluorophore, creating an excited electronic singlet state ($S_1'$). This process distinguishes fluorescence from chemiluminescence, in which the excited state is populated by a chemical reaction.

The second, excited state exists for a finite time (typically 1-10 nanoseconds). During this time, the fluorophore undergoes conformational changes and is also subject to a multitude of possible interactions with its molecular environment. These processes have two important consequences. First, the energy of $S_1'$ is partially dissipated, yielding a relaxed singlet excited state ($S_1$) from which fluorescence emission originates. Second, not all the molecules initially excited by absorption (stage 1) return to the ground state ($S_0$) by fluorescence emission. Other processes such as collisional quenching, fluorescence resonance energy transfer (FRET) and intersystem crossing may also depopulate $S_1$. The fluorescence quantum yield, which is the ratio of the number of fluorescence photons emitted (stage 3) to the number of photons absorbed (stage 1), is a measure of the relative extent to which these processes occur.

In the third stage, a photon of energy $h\nu_{EM}$ is emitted, returning the fluorophore to its ground state $S_0$. Due to energy dissipation during the excited-state lifetime, the energy of this photon is lower, and therefore of longer wavelength, than the excitation photon $h\nu_{EX}$. The difference in wavelengths between the peak excitation and emission of a fluorescent species represented by ($h\nu_{EX}-h\nu_{EM}$) is called the Stokes shift.

The Stokes shift is fundamental to the sensitivity of fluorescence techniques because it allows emission photons to be detected against a low background, isolated from excitation photons.

The entire fluorescence process is cyclical. Unless the fluorophore is irreversibly destroyed in the excited state (an important phenomenon known as photobleaching), the same fluorophore can be excited and detected repeatedly. The fact that a single fluorophore can generate many thousands of detectable photons is fundamental to the high sensitivity of fluorescence detection techniques. For polyatomic molecules in solution, the discrete electronic transitions represented by $h\nu_{EX}$ and $h\nu_{EM}$ are replaced by rather broad energy spectra called the fluorescence excitation spectrum and fluorescence emission spectrum, respectively. The bandwidths of these spectra are parameters of particular importance for applications in which two or more different fluorophores are simultaneously detected. With few exceptions, the fluorescence excitation spectrum of a single fluorophore species in dilute solution is identical to its absorption spectrum. Under the same conditions, the fluorescence emission spectrum is independent of the excitation wavelength, due to the partial dissipation of excitation energy during the excited-state lifetime. The emission intensity is proportional to the amplitude of the fluorescence excitation spectrum at the excitation wavelength.

The term "fluorescence emission activity" as used interchangeably with "fluorescence intensity" in accordance with the present invention means the fluorescence intensity at one or more wavelength(s) up to the entire emission spectrum which results from an excitation at the appropriate wavelength(s). Depending on further mutations effected to the nucleic acid molecule of the present invention, the maximum emission activity can slightly alter. For example, the useful range of maximum emission wavelengths could be from 505 to 515 nm, in particular at any one of 505, 506, 507, 508, 509, 510, 511, 512, 513, 514 and 515 nm. In a preferred embodiment, the maximum emission wavelength is 509 nm.

The term "hybridizes/hybridizing" as used herein refers to a pairing of a nucleic acid molecule to a (partially) complementary strand of this nucleic acid molecule which thereby form a hybrid.

It is well known in the art how to perform hybridization experiments with nucleic acid molecules. Correspondingly, the person skilled in the art knows what hybridization conditions she/he has to use to allow for a successful hybridization in accordance with item (c), above. The establishment of suitable hybridization conditions is referred to in standard text books such as Sambrook, Russell "Molecular Cloning, A Laboratory Manual", Cold Spring Harbor Laboratory, N.Y. (2001); Ausubel, "Current Protocols in Molecular Biology", Green Publishing Associates and Wiley Interscience, N.Y. (1989), or Higgins and Hames (Eds.) "Nucleic acid hybridization, a practical approach" IRL Press Oxford, Washington D.C., (1985).

"Stringent conditions" refers to hybridization conditions under which the polynucleotides that are capable of hybridizing to the nucleic acids of the invention or parts thereof hybridize to these target sequences to a detectably greater degree than to other sequences (e.g., at least 2-fold over background). Stringent conditions are sequence-dependent and will be different in different circumstances. By controlling the stringency of the hybridization and/or washing conditions, target sequences that have at least 90% sequence identity, more preferably 95%, such as 98% and more preferred 100% sequence identity to the probe can be identified (highly stringent hybridization conditions). Alternatively, stringency conditions can be adjusted to allow a higher degree of mismatching in sequences (low stringency conditions of hybridization). Such highly stringent and low stringent conditions for hybridization are well known to the person skilled in the art.

For example "stringent conditions" refers to hybridization conditions which comprise, e.g. an overnight incubation at 65° C. in 4×SSC (600 mM NaCl, 60 mM sodium citrate) followed by washing at 65° C. in 0.1×SSC for one hour. Alternatively, hybridization conditions can comprise: an overnight incubation at 42° C. in a solution comprising 50% formamide, 5×SSC (750 mM NaCl, 75 mM sodium citrate), 50 mM sodium phosphate (pH 7.6), 5×Denhardt's solution, 10% dextran sulphate, and 20 µg/ml denatured, sheared salmon sperm DNA, followed by washing in e.g. 0.1-0.5× SSC at about 55-65° C. for about 5 to 20 min. Said conditions for hybridization are also known by a person skilled in the art as "highly stringent conditions for hybridization". It is of note that variations in the above conditions may be accomplished through the inclusion and/or substitution of alternate blocking reagents. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility. Such modifications can generally be effected by the skilled person without further ado.

A hybridization complex may be formed in solution (e.g., Cot or Rot analysis) or between one nucleic acid sequence present in solution and another nucleic acid sequence immobilized on a solid support (e.g., membranes, filters, chips, pins or glass slides to which, e.g., cells have been fixed).

Examples for hybridization assays comprise without limitation Northern and Southern blot assays, heteroduplex analysis, detection of mutations by sequence specific oligonucleotide hybridization, allele-specific oligonucleotide hybridization on DNA chips, assays based on the Illumina's® technology, assays based on the BeadArray® technology, see, for example, Barnes et al., Nucleic Acids Res. 33 (2005) 5914-5923; Fan et al., Biotechniques 39 (2005) 583-588; Shen et al., Mutat. Res.-Fund. Mol. M. 573 (2005) 70-82; Steemers and Gunderson, Pharmacogenomics, 6 (2005) 777-782.

The term "degenerate" in accordance with the present invention refers to the degeneracy of the genetic code. Degeneracy results because a triplet code designates 20 amino acids and a stop codon. Because four bases exist which are utilized to encode genetic information, triplet codons are required to produce at least 21 different codes. The possible $4^3$ possibilities for bases in triplets gives 64 possible codons, meaning that some degeneracy must exist. As a result, some amino acids are encoded by more than one triplet, i.e. by up to six. The degeneracy mostly arises from alterations in the third position in a triplet. This means that nucleic acid molecules having a different sequence than that specified above, but still encoding the same polypeptide lie within the scope of the present invention.

The present invention provides novel engineered variants of the enhanced green fluorescent protein (eGFP). Experimentally, the variants have been generated by somatic hypermutation and directed evolution in the chicken B cell line DT40 (growing at 41° C.) starting with the amino acid sequence of eGFP (Cormack et al., 1996). The eGFP sequence used in the present invention has one additional codon (Val) inserted next to the start codon, as compared to the wild-type sequence published according to Prasher et al. (1992), to yield an optimal translation-initiation sequence (Kozak motif). This Val was numbered as codon 1a in FIG. 2 according to the numbering scheme used in Tsien (1998) for the easier comparison to wild-type GFP and previously reported GFP mutants. In the appended sequence listing, this amino acid was termed aa 2 (instead of 1a as in FIG. 2) so that all following amino acids in the sequences are shifted by one position, as compared to the sequence numbering in Tsien (1998). Thus, in the present invention, e.g. the mutation Y145F according to the numbering scheme in Tsien (1998) corresponds to Y146F and S202T corresponds to S203T in the sequence used in the present invention. The same numbering principle applies to mutations described hereinafter.

The GFP variant of the present invention exhibits enhanced fluorescence in the same spectral range relative to eGFP when expressed in eukaryotic cells and is more stable at temperatures up to 41° C. The modified GFP protein further provides a means for detecting GFP probes, i.e. proteins comprising the GFP variant of the invention, in eukaryotic cells grown at temperatures up to 41° C. and/or at lower levels of expression having an increased sensitivity relative to eGFP. This greatly improves the usefulness of fluorescent proteins in studying cellular functions in living cells.

Despite the high number of mutations known and effected, a GFP variant satisfying the need for a probe with enhanced fluorescence intensity without a shift in the absorption and/or emission spectrum could not be obtained in the prior art.

Whereas some of the mutations found in accordance with the invention were individually known in the art, the increase in fluorescence intensity conferred by the combination of mutations forming the basis of the invention must therefore be viewed as surprising. Although the Y145F mutation has been reported to contribute to an increase in the fluorescence intensity in the art, the reported increase was affected in blue or cyan variants such as P4-3 or EBFP (Heim and Tsien, 1996; Yang et al. 1998). Furthermore, the Y145F mutation in combination with Y66H is supposed to be responsible for shifts in the excitation and/or emission spectra so that a variant comprising this mutation but having the same spectra could not reasonably be expected. More importantly, in view of the prior art, it is particularly surprising that a mutation at position 202 occupied by serine in eGFP, could contribute in a GFP variant with further increased fluorescence intensity. Namely and as discussed above, S202F was shown to eliminate excitation at 475 nm and, in combination with T203I, was shown to not alter the properties of GFP. This finding was confirmed as illustrated in the appended examples where S202T in combination with the neutral to slightly less bright mutant Q80E actually decreases the intensity of eGFP. Thus, whereas the Y145F (Y146F in the present invention) mutation had been described in blue or cyan variants before, there was no expectation whatsoever that the combination of the Y145F and S202T (S203T in the present invention) mutations could enhance the fluorescence intensity beyond that of an eGFP carrying only the Y145F mutation and certainly not by the factor of 2.5 as compared to eGFP (see table 2) while at the same time preserving the maximum excitation and emission wavelength(s) of eGFP. The amino acids present in the chromophore determine the absorption and emission spectrum of fluorescent proteins derived from Aequorea victoria. Thus, the mutations present in the GFP variants of the present invention in general comprise a chromophore formed by amino acids T66, Y67 and G68. The enhanced fluorescence emission of the GFP variant of the present invention opens up the possibility to assess in vivo data without sacrificing animals. A useful example would be to label stem cells with the GFP variant of the invention which are to be transplanted e.g. into the eye of animals to track stem cell migration and colonization of tissues in vivo.

In a preferred embodiment in the nucleic acid molecule encoding a polypeptide having the amino acid sequence of SEQ ID NO: 2, alanine replaces valine at position 164 in addition to the mutations Y146F and S203T.

V163A (V164A in the present invention) is known to enhance the fluorescence intensity of a GFP comprising the S65T mutation and to increase its temperature tolerance. The triple mutation as compared to the eGFP used as starting material shows an even more enhanced fluorescence intensity by the factor of 3.2 as compared to eGFP (see table 2). The nucleic acid and amino acid sequences of this GFP variant are depicted in SEQ ID NOs: 3 and 4, respectively.

In another preferred embodiment, in the nucleic acid molecule encoding a polypeptide having the amino acid sequence of SEQ ID NO: 2 valine replaces leucine at position 222 in addition to the mutations Y146F and S203T and optionally V164A. The nucleic acid and amino acid sequences of this GFP variant are depicted in SEQ ID NOs: 5 and 6 (Y146A, S203T and L222V) and SEQ ID NOs: 7 and 8 (Y146, S203T, V164A and L222V), respectively.

The amino acid substitution L221V (L222V in the present invention) is localized in a region known to influence GFP dimerization and its effect on the fluorescence intensity of the GFP variant of the present invention might be due to the enhancement of dimer formation as opposed to the mutation L221K (Zacharias et al, 2002) which was shown to eliminate dimerization of GFP but not to have any effect on the brightness of the resulting variant. The presence of the L222V mutation further enhances the fluorescence intensity by the factor of 3.3 as compared to eGFP (see table 2). However, dimerization would be expected to substantially increase fluorescence more than is seen with the L221V mutation in comparison to the variant without this mutation (e.g. SEQ ID NOs: 3 or 4).

In another preferred embodiment, the nucleic acid molecule is DNA.

The present invention also relates to a vector comprising the nucleic acid molecule of the present invention. Preferably, the vector is a plasmid, cosmid, virus, bacteriophage or another vector used conventionally e.g. in genetic engineering.

The nucleic acid molecule of the present invention may be inserted into several commercially available vectors. Non-limiting examples include prokaryotic plasmid vectors, such as the pUC-series, pBluescript (Stratagene), the pET-series of expression vectors (Novagen) or pCRTOPO (Invitrogen), lambda gt11, pJOE, the pBBR1-MCS series, pJB861, pBSMuL, pBC2, pUCPKS, pTACT1 and vectors compatible with expression in mammalian cells like pREP (Invitrogen), pCEP4 (Invitrogen), pMC1 neo (Stratagene), pXT1 (Stratagene), pSG5 (Stratagene), EBO-pSV2neo, pBPV-1, pdBPVMMTneo, pRSVgpt, pRSVneo, pSV2-dhfr, pIZD35, Okayama-Berg cDNA expression vector pcDV1 (Pharmacia), pRc/CMV, pcDNA1, pcDNA3 (Invitrogene), pSPORT1 (GIBCO BRL), pGEMHE (Promega), pLXIN, pSIR (Clontech), pIRES-EGFP (Clontech), pEAK-10 (Edge Biosystems) pTriEx-Hygro (Novagen) and pCINeo (Promega). Examples for plasmid vectors suitable for *Pichia pastoris* comprise e.g. the plasmids pAO815, pPIC9K and pPIC3.5K (all Invitrogen).

The nucleic acid molecule of the present invention referred to above may also be inserted into vectors such that a translational fusion with another nucleic acid molecule is generated. The other nucleic acid molecules may encode a protein which may e.g. increase the solubility and/or facilitate the purification of the protein encoded by the nucleic acid molecule of the invention. Non-limiting examples include pET32, pET41, pET43. The vectors may also contain an additional expressible polynucleotide coding for one or more chaperones to facilitate correct protein folding. Suitable bacterial expression hosts comprise e.g. strains derived from BL21 (such as BL21(DE3), BL21(DE3)PlysS, BL21(DE3) RIL, BL21(DE3)PRARE) or Rosetta®.

For vector modification techniques, see Sambrook and Russel, 2001. Generally, vectors can contain one or more origins of replication (ori) and inheritance systems for cloning or expression, one or more markers for selection in the host, e.g., antibiotic resistance, and one or more expression cassettes. Suitable origins of replication include, for example, the Col E1, the SV40 viral and the M13 origins of replication.

The coding sequences inserted in the vector can e.g. be synthesized by standard methods, or isolated from natural sources. Ligation of the coding sequences to transcriptional regulatory elements and/or to other amino acid encoding sequences can be carried out using established methods. Transcriptional regulatory elements (parts of an expression cassette) ensuring expression in prokaryotes or eukaryotic cells are well known to those skilled in the art. These elements comprise regulatory sequences ensuring the initiation of the transcription (e.g., translation initiation codon, promoters, enhancers, and/or insulators), internal ribosomal entry sites (IRES) (Owens et al., 2001) and optionally poly-A signals ensuring termination of transcription and stabilization of the transcript. Additional regulatory elements may include transcriptional as well as translational enhancers, and/or naturally-associated or heterologous promoter regions. Preferably, the nucleic acid molecule of the invention is operably linked to such expression control sequences allowing expression in prokaryotes or eukaryotic cells. The vector may further comprise nucleotide sequences encoding secretion signals as further regulatory elements. Such sequences are well known to the person skilled in the art. Furthermore, depending on the expression system used, leader sequences capable of directing the expressed polypeptide to a cellular compartment may be added to the coding sequence of the nucleic acid molecule of the invention. Such leader sequences are well known in the art. Specifically-designed vectors allow the shuttling of DNA between different hosts, such as bacteria-fungal cells or bacteria-animal cells.

An expression vector according to this invention is capable of directing the replication, and the expression of the nucleic acid molecule of the invention and the polypeptide encoded thereby.

The nucleic acid molecules of the invention as described herein above may be designed for direct introduction or for introduction via liposomes, phage vectors or viral vectors (e.g. adenoviral, retroviral) into the cell. Additionally, baculoviral systems or systems based on Vaccinia Virus or Semliki Forest Virus can be used as vector in eukaryotic expression system for the nucleic acid molecules of the invention. Expression vectors derived from viruses such as retroviruses, vaccinia virus, adeno-associated virus, herpes viruses, or bovine papilloma virus, may be used for delivery of the polynucleotides or vector into targeted cell population. Methods which are well known to those skilled in the art can be used to construct recombinant viral vectors; see, for example, the techniques described in Sambrook, 2001 and Ausubel, 2001.

A typical mammalian expression vector contains the promoter element, which mediates the initiation of transcription of mRNA, the protein coding sequence, and signals required for the termination of transcription and polyadenylation of the transcript. Moreover, elements such as origin of replication, drug resistance gene, regulators (as part of an inducible promoter) may also be included. The lac promoter is a typical inducible promoter, useful for prokaryotic cells, which can be induced using the lactose analogue isopropylthiol-b-D-galactoside. ("IPTG"). For recombinant expression, the antibody fragment may be ligated between e.g. the PelB leader signal, which directs the recombinant protein in the periplasm and the gene III in a phagemid called pHEN4 (described in Ghahroudi et al, 1997). Additional elements might include enhancers, Kozak sequences and intervening sequences flanked by donor and acceptor sites for RNA splicing. Highly efficient transcription can be achieved with the early and late promoters from SV40, the long terminal repeats (LTRs) from retroviruses, e.g., RSV, HTLVI, HIVI, and the early promoter of the cytomegalovirus (CMV). However, cellular elements can also be used (e.g., the human actin promoter). The co-transfection with a selectable marker such as dhfr, gpt, neomycin, hygromycin allows the identification and isolation of the transfected cells. The transfected nucleic acid can also be amplified to express large amounts of the encoded (poly) peptide. The DHFR (dihydrofolate reductase) marker is useful to develop cell lines that carry several hundred or even several thousand copies of the gene of interest. Another useful selection marker is the enzyme glutamine synthase (GS) (Murphy et al. 1991; Bebbington et al. 1992). Using these markers, the mammalian cells are grown in selective medium and the cells with the highest resistance are selected. As indicated above, the expression vectors will preferably include at least one selectable marker. Such markers include dihydrofolate reductase, G418 or neomycin resistance for eukaryotic cell culture and tetracycline, kanamycin or ampicillin resistance genes for culturing in E. coli and other bacteria.

Possible regulatory elements permitting expression in prokaryotic host cells comprise, e.g., the lac, trp or tac promoter, the lacUV5 or the trp promotor in E. coli, and examples for regulatory elements permitting expression in eukaryotic host cells (the more preferred embodiment) are the AOX1 or GAL1 promoter in yeast or the CMV- (Cytomegalovirus), SV40-, RSV-promoter (Rous sarcoma virus), chicken beta-actin promoter, CAG-promoter (a combination of chicken beta-actin promoter and cytomegalovirus immediate-early enhancer), the gai10 promoter, human elongation factor 1α-promoter, CMV enhancer, CaM-kinase promoter, the *Autographa californica* multiple nuclear polyhedrosis virus (AcMNPV) polyhedral promoter or a globin intron in mammalian and other animal cells. Besides elements which are responsible for the initiation of transcription such regulatory elements may also comprise transcription termination signals, such as the SV40-poly-A site or the tk-poly-A site or the SV40, lacZ and AcMNPV polyhedral polyadenylation signals, downstream of the polynucleotide.

In another embodiment, the present invention relates to a non-human host transformed with the vector of the invention.

Non-human hosts according to the invention can be single cells or multi-cellular organisms.

Suitable prokaryotic hosts comprise e.g. bacteria of the species *Escherichia, Streptomyces, Salmonella* or *Bacillus*. Suitable eukaryotic host cells are e.g. yeasts such as *Saccharomyces cerevisiae* or *Pichia pastoris*. Insect cells suitable for expression are e.g. *Drosophila* S2 or *Spodoptera* Sf9 cells.

Mammalian host cells that could be used include, human Hela, HEK293, H9 and Jurkat cells, mouse NIH3T3 and C127 cells, COS 1, COS 7 and CV1, quail QC1-3 cells, mouse L cells, Bowes melanoma cells and Chinese hamster ovary (CHO) cells. Also within the scope of the present invention are primary mammalian cells or cell lines. Primary cells are cells which are directly obtained from an organism. Suitable primary cells are, for example, mouse embryonic fibroblasts (MEF), mouse primary hepatocytes, cardiomyocytes and neuronal cells as well as mouse muscle stem cells (satellite cells) and stable, immortalized cell lines derived thereof. Alternatively, the recombinant protein of the invention can be expressed in stable cell lines that contain the gene construct integrated into a chromosome.

Appropriate culture media and conditions for the above-described host cells are known in the art.

Transgenic non-human animals as hosts transfected with and/or expressing the nucleic acid molecule of the present invention also lie within the scope of the invention. In a preferred embodiment, the transgenic animal is a mammal, e.g. a hamster, mouse, rat, cow, cat, pig, dog, horse, rabbit or monkey.

Transgenic plants as hosts transfected with and/or expressing the nucleic acid molecule of the present invention also lie within the scope of the present invention.

A method for the production of a transgenic non-human animal, for example a transgenic mouse, comprises introduction of the nucleic acid molecule or targeting vector of the present invention into a germ cell, an embryonic cell, stem cell or an egg or a cell derived therefrom. The non-human animal can be used in accordance with the invention e.g. in a method for identification of compounds, described herein below. Production of transgenic embryos and screening of those can be performed, e.g., as described by A. L. Joyner Ed., Gene Targeting, A Practical Approach (1993), Oxford University Press. The DNA of the embryonic membranes of embryos can be analyzed using, e.g., Southern blots with an appropriate probe; see supra. A general method for making transgenic non-human animals is described in the art, see for example WO 94/24274. For making transgenic non-human organisms (which include homologously targeted non-human animals), embryonal stem cells (ES cells) are preferred. Murine ES cells, such as AB-1 line grown on mitotically inactive SNL76/7 cell feeder layers (McMahon and Bradley, Cell 62:1073-1085 (1990)) essentially as described (Robertson, E. J. (1987) in Teratocarcinomas and Embryonic Stem Cells: A Practical Approach. E. J. Robertson, ed. (Oxford: IRL Press), p. 71-112) may be used for homologous gene targeting. Other suitable ES lines include, but are not limited to, the E14 line (Hooper et al., Nature 326:292-295 (1987)), the D3 line (Doetschman et al., J. Embryol. Exp. Morph. 87:27-45 (1985)), the CCE line (Robertson et al., Nature 323:445-448 (1986)), the AK-7 line (Zhuang et al., Cell 77:875-884 (1994)). The success of generating a mouse line from ES cells bearing a specific targeted mutation depends on the pluripotence of the ES cells (i.e., their ability, once injected into a host developing embryo, such as a blastocyst or morula, to participate in embryogenesis and contribute to the germ cells of the resulting animal). The blastocysts containing the injected ES cells are allowed to develop in the uteri of pseudopregnant non-human females and are born, e.g. as chimeric mice. The resultant transgenic mice are chimeric for cells having either the recombinase or reporter loci and are backcrossed and screened for the presence of the correctly targeted transgene(s) by PCR or Southern blot analysis on tail biopsy DNA of offspring so as to identify transgenic mice heterozygous for either the recombinase or reporter locus/loci.

In yet another embodiment, the present invention relates to a method of producing a polypeptide comprising culturing the host of the invention under suitable conditions and isolating the polypeptide produced.

Suitable conditions for culturing a prokaryotic or eukaryotic host are well known to the person skilled in the art. For example, suitable conditions for culturing bacteria are growing them under aeration in Luria Bertani (LB) medium. To increase the yield and the solubility of the expression product, the medium can be buffered or supplemented with suitable additives known to enhance or facilitate both. E. coli can be cultured from 4 to about 37° C., the exact temperature or sequence of temperatures depends on the molecule to be overexpressed. In general, the skilled person is also aware that these conditions may have to be adapted to the needs of the host and the requirements of the polypeptide expressed. In case an inducible promoter controls the nucleic acid of the invention in the vector present in the host cell, expression of the polypeptide can be induced by addition of an appriopriate inducing agent. Suitable expression protocols and strategies are known to the skilled person.

Depending on the cell type and its specific requirements, mammalian cell culture can e.g. be carried out in RPMI or DMEM medium containing 10% (v/v) FCS, 2 mM L-glutamine and 100 U/ml penicillin/streptomycine. The cells can be kept at 37° C. in a 5% $CO_2$, water saturated atmosphere.

Suitable media for insect cell culture is e.g. TNM+10% FCS or SF900 medium. Insect cells are usually grown at 27° C. as adhesion or suspension culture.

Suitable expression protocols for eukaryotic cells are well known to the skilled person and can be retrieved e.g. from in Sambrook, 2001.

Methods of isolation of the polypeptide produced are well-known in the art and comprise without limitation method steps such as ion exchange chromatography, gel filtration chromatography (size exclusion chromatography), affinity chromatography, high pressure liquid chromatography (HPLC), reversed phase HPLC, disc gel electrophoresis or immunoprecipitation, see, for example, in Sambrook, 2001.

The present invention also relates to a polypeptide comprising the amino acid sequence encoded by a nucleic acid molecule of the present invention or obtainable by the method of the present invention.

The present invention furthermore relates to a fusion protein. In addition to the sequence of the GFP variant of the present invention, a fusion protein according to the present invention contains at least one additional, heterologous sequence. Often, but not necessarily, these additional sequences will be located at the N- or C-terminal end of the polypeptide. It may e.g. be convenient to initially express the polypeptide as a fusion protein from which the additional amino acid residues can be removed, e.g. by a proteinase capable of specifically trimming the polypeptide of the present invention. The additional heterologous sequences may help in the expression or purification or attachment to a carrier of the polypeptides referred to in the present invention. The GFP variant of the present invention could also be fused to a protease cleavage sequence and a quencher that when cleaved allows identification by increase in fluorescence.

In a preferred embodiment, the polypeptide of the invention is fused to one or more selected from e.g. tags or signal sequences. Both are conveniently used to facilitate expression and/or purification of proteins. Examples include a His-tag, a Strep-tag, a GST-tag, a TAP tag (tandem affinity purification tags), biotinylation using the bir BAD system (biotinylation acceptor domain), an HA tag, a signal sequence for intra- or extracellular targeting, e.g. nuclear localisation signals (NLS; e.g. PPKKKRKV)(SEQ ID NO:24), signals to retain a protein in the endoplasmatic reticulum (e.g. KDEL)(SEQ ID NO:25), peroxisomes (e.g. SKL), secretion signals or signals for trans-Golgi-network sorting.

Further preferred proteins to be combined with the polypeptide of the present invention and optionally the tags and signal sequences as described above are in general proteins the presence or localization of which in cells and/or tissues is to be investigated. Exemplary proteins are those forming the cytoskeleton or proteins forming part of a signal transduction pathway or membrane proteins binding to one or more ligands, e.g. for studying the effects of drugs, receptor-ligand binding, proteins tagged for RNAi studies, protease activity, cell differentiation or proteins attached to nano-probes and quantum dots. Useful assays for the GFP variant of the present invention are e.g. FRET assays or two-hybrid assays. In general, the GFP variant of the present invention is useful as a biomarker and in diagnostics.

The invention furthermore relates to a diagnostic composition comprising at least one of
(a) the nucleic acid molecule of the invention,
(b) the vector of the invention,
(c) the polypeptide of the invention or
(d) the fusion protein of the invention.

The present invention furthermore relates to a method of detecting the expression of a gene of interest, comprising
(a) operably linking the nucleic acid molecule of the invention with a promoter controlling said gene of interest or
(a)' fusing the nucleic acid molecule of the invention to said gene of interest and
(b) detecting the fluorescence of the protein encoded by said nucleic acid molecule.

Four essential elements of fluorescence detection systems can be identified: 1) an excitation source, 2) a fluorophore, 3) wavelength filters to isolate emission photons from excitation photons and 4) a detector that registers emission photons and produces a recordable output, usually as an electrical signal or a photographic image. Regardless of the application, compatibility of these four elements is essential for optimizing fluorescence detection.

Fluorescence instruments are primarily of four types, each providing distinctly different information: Spectrofluorometers and microplate readers measure the average properties of bulk (μL to mL) samples. Fluorescence microscopes resolve fluorescence as a function of spatial coordinates in two or three dimensions for microscopic objects (less than ~0.1 mm diameter).

Fluorescence scanners, including microarray readers, resolve fluorescence as a function of spatial coordinates in two dimensions for macroscopic objects such as electrophoresis gels, blots and chromatograms.

Flow cytometers measure fluorescence per cell in a flowing stream, allowing subpopulations within a large sample to be identified and quantitated.

Other types of instrumentation that use fluorescence detection include capillary electrophoresis apparatus, DNA sequencers and microfluidic devices. Each type of instrument produces different measurement artefacts and makes different demands on the fluorescent probe. For example, although photobleaching is often a significant problem in fluorescence microscopy, it is not a major impediment in flow cytometry or DNA sequencers because the dwell time of individual cells or DNA molecules in the excitation beam is short.

In accordance with the present invention and depending on the demands and possibilities of the methods described herein, the overall fluorescence can be detected in a sample as well as the location of the fluorescence within a sample.

A reporter gene is a gene that can be operably linked to a gene of interest or simply to a promoter controlling the gene of interest in cell culture, animals or plants. Reporter genes are e.g. used to determine whether the gene of interest has been taken up by or expressed in the cell or organism population or whether the gene of interest naturally present in the cell or organism is expressed. It is important to use a reporter gene that is not natively expressed in the cell or organism under study, since the expression of the reporter is being used as a marker. The nucleic acid of the present invention encodes a GFP variant suitable as reporter gene with advantageous properties as described above.

To introduce a reporter gene into an organism, the reporter gene and the gene of interest are placed in the same DNA construct to be inserted into the cell or organism, most often as a plasmid. Reporter genes can also be used to assay for the expression of the gene of interest, which may produce a protein that has little obvious or immediate effect on the cell culture or organism. In these cases the reporter is directly attached to the gene of interest to create a gene fusion. The two genes are under the control of the same promoter and are transcribed into a single messenger RNA molecule (mRNA). The mRNA is then translated into protein. In these cases it is important that both proteins be able to properly fold into their active conformations and interact with their substrates despite being fused. Methods to determine whether this is the case are well-known to the skilled person. In building the DNA construct, a segment of DNA coding for a flexible polypeptide linker region is usually included so that the reporter and the gene product of will only minimally interfere with one another.

In addition, the present invention relates to a method of detecting the activity of a promoter of interest, comprising operably linking the nucleic acid molecule of the invention with said promoter of interest and detecting the fluorescence of the protein encoded by said nucleic acid molecule.

The analysis of the activity of promoters, which has been proven to be a highly sensitive and time-saving technique, is widely used e.g. in the study of transcriptional regulation.

Reporter genes can also be used to assay for the activity of a particular promoter in a cell or organism. In this case the reporter gene is simply placed under the control of the target promoter and the reporter gene product's activity is quantitatively measured. The results are normally reported relative to the activity under a "consensus" promoter known to induce strong gene expression.

The skilled person is well aware of promoter and reporter assays the principles of which are commonly known in the art (see e.g. Lewin, Genes IX or Sambrook et al., Molecular Cloning).

Random introduction of the GFP into the chromosome can be used to identify promoters. Luciferase or beta-gal is usually used to do this as previously fluorescent proteins were not bright enough to detect weak promoter activity. This would also facilitate the usage of weak promoters needed to express fusion proteins that could be toxic to the cell at higher expression levels. A brighter GFP variant would allow the detection of lowly expressed fusion products.

Furthermore, the present invention relates to a method of detecting the presence of a protein of interest, comprising contacting a sample with the fusion protein of the invention, wherein said fusion protein comprises a polypeptide specifically binding to the protein of interest.

The method of the invention can be carried out using FAC scans and preparative FAC sorts.

A sample can be any matter potentially containing the protein of interest. Preferred samples are liquids, e.g. cellular extracts or supernatants of cell cultures, or samples comprising living or dead cells in single form or present as a tissue or organ.

Contacting a sample in accordance with the present invention means bringing the sample into contact with the fusion protein of the invention. The term comprises bringing both components into close vicinity as well as e.g. transforming or transfecting cells with a nucleic acid molecule encoding the fusion protein of the invention in order to express the fusion protein in the cells.

Specifically binding in accordance with the present invention refers to the property of certain proteins to have an affinity for specific proteins, i.e. target proteins, which is greater by the factor of at least 10, preferably at least 100, more preferably at least 1000 and most preferably at least 10000 as compared to the affinity to proteins unrelated to the target protein. These proteins can e.g. be natural interaction partners of the target protein including proteins interacting in the course of signal transduction pathways or in context with structural proteins or antibodies.

The present invention furthermore relates to a method of detecting the localization of a fusion protein of the present invention or a fusion protein comprising the polypeptide of the present invention in a cell or tissue, comprising exciting said fusion protein or polypeptide and detecting the location of the fluorescence emitted by the excited fusion protein or polypeptide.

The present method can be used to localize the fusion protein of the invention as well as interaction partners of the fusions proteins of the invention.

The methods of the present invention are also suitable in the identification of compounds influencing e.g. the expression of target genes, the location of target proteins or the activity of target proteins. Said compounds may then be contacted, at the same time or separately, with a cell comprising the nucleic acid of the invention, e.g. fused to a target gene or a regulatory sequence. Afterwards, expressed (fusion) protein is excited in a cell contacted with the compound(s) and in a cell which has not been contacted. The expression or location of the (fusion)protein in both cells is compared, wherein a difference observed in the expression or location in both cells indicates that the compound has an influence on the expression of target genes and/or the location or activity of target proteins.

Finally, the present invention relates to a kit comprising at least one of
(a) the nucleic acid molecule of the invention
(b) the vector of the invention
(c) the host of the invention
(d) the polypeptide of the invention or
(e) the fusion protein of the invention.

The various components of the kit may be packaged in one or more containers such as one or more vials. The vials may, in addition to the components, comprise preservatives or buffers for storage.

The figures show:

FIG. 1: Strategy for artificial evolution of eGFP gene (A) A physical map of the chicken rearranged Ig light chain locus, the pHypermut1-eGFP targeting construct and the rearranged Ig light chain locus after targeted integration and marker excision is shown. The positions of primers used for the identification of targeted integration events are shown by arrows. (B) FACS profiles of $AID^{R1}IgL^{eGFP1}$ and $AID^{-/-}IgL^{eGFP1}$ clones. The average percentages of events falling into the $GFP^{high}$ and $GFP^{low}$ gates based on the measurement of 24 subclones are shown. (C) Sorting strategy for cells of increased fluorescence activity.

FIG. 2: Mutations downstream and within the eGFP transgene.

(A) Mutations identified at the exon/intron border of the Ig light chain leader sequence. The number of times a mutation was found is shown by superscript. (SEQ ID NO:26). (B) Mutations within the eGFP sequence (SEQ ID NOs:1-2) together with the corresponding amino acid codons. Mutations were mapped below the reference eGFP sequence together with the corresponding amino acid codons. The eGFP sequence which we used had one codon (Val) inserted next to the start codon to yield an optimal translation-initiation sequence (Kozak motif). This Val was numbered as codon 1a according to Crameri et al. (1996) or Tsien (1998) for the easier comparison to wild-type GFP and previously reported GFP mutants. (C) Pedigrees for the evolution of the eGFP transgenes in culture. The number of times each sequence was found within each subclone is indicated at the right side of the circles. The amino acid changes of each step are shown beside the arrows. Sequences identified in more than one subclone are named v1-v9.

Figure 3A:
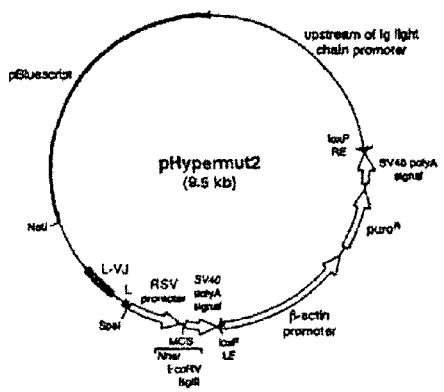

FIG. 3: Hypermutation of transgenes using pHypermut2

(A) Plasmid map of pHypermut2 vector. Target genes for artificial evolution can be cloned into the NheI, EcoRV or BglII sites. Potential gene conversion donor sequences can be cloned into the SpeI site. (B) A physical map of the rearranged Ig light chain locus, the pHypermut2-eGFP construct and the rearranged Ig light chain locus after targeted integration. The positions of primers used for the identification of targeted integration events are shown by arrows. (C) FACS profile of the $\Psi V^- AID^{R1} IgL^{eGFP}$ clone having integrated the pHypermut2-eGFP construct into the rearranged Ig light chain locus after two weeks culture. The average percentage of events falling into the $GFP^{low}$ gate based on the measurement of 24 subclones is shown.

FIG. 4: Analysis of variant GFP transfectants.

(A) FACS analysis of control and variant GFP transfectants. The average fluorescence of $AID^{-/-}IgL^{eGFP}$ is indicated by a green guideline for easier comparison. (B) Relative fluorescence of the transfectants normalized to the fluorescence of $AID^{-/-}IgL^{eGFP}$. (C) Excitation and emission spectra. (D) Image of single cells by fluorescence microscopy. The image of the same single cells is shown with fluorescence activation (upper row) and without fluorescence activation (lower row).

Figure 5:
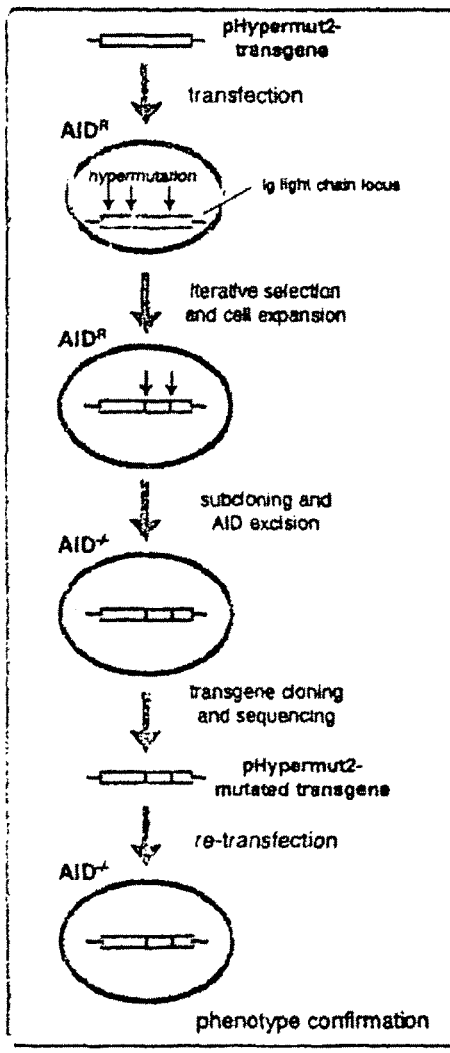

FIG. 5: Scheme of artificial evolution in DT40.

The approach only requires a cell line like $AID^R$ which conditionally expresses AID and the pHypermut2 targeting vector.

The Sequence Listing submitted herewith in computer readable form is incorporated herein by reference.

The examples illustrate the invention.

EXAMPLE 1

Materials and Methods

Cell lines. The DT40 clones, $AID^{R1}CL1$ and $AID^{R1}CL2$, were derived from $DT40^{Cre1}AID^{-/-}$ (16) by stable transfection of a floxed AID-IRES (internal ribosome entry site)-gpt (guanine phosphoribosyl transferase) bicistronic cassette, in which both AID and gpt are expressed from the same β-actin promoter. Transfectants which had integrated the pHypermut1- or pHypermut2-derived targeting vectors into the rearranged Ig light chain locus were identified by PCR using primer pairs P1/P2 and P1/P3, respectively. To confirm vector integration into the rearranged Ig light chain locus, the presence of the VJ intervening sequence from the non-rearranged locus was confirmed by PCR using primer pairs of P4/P5. Cell culture and electroporation conditions were previously described (Arakawa et al., 2002).

Flow cytometry. Subcloning and FACS sorting have been described previously (Arakawa et al., 2002). Preparative FACS sorting was performed by the MoFlo high-speed cell sorter (Cytomation).

PCR, cloning and sequencing. PCR was performed as previously described (Arakawa et al., 2002). The eGFP gene of sorted cells was amplified from genomic DNA template using primer pair P6/P7. The PCR products were digested with HindIII and XbaI, cloned into the pUC119 plasmid vector and sequenced using primers P8 and P9. To confirm the phenotypes of the mutated eGFP by retransfection, the genes were amplified using PfuUltra hotstart polymerase (Stratagene) and primer pair P10/P11, digested by AvrII and cloned into the NheI site of pHypermut2. The mutant eGFPs in pHypermut2 were verified by sequencing using primers P12 and P13.

Site-directed mutagenesis. To combine codon changes found in different eGFP variants, we designed primers which included the intended mutations in the center of the primer sequence. In the first step parts of the eGFP gene were amplified by PCR using at least one mutation-containing primer. In the second step PCR fragments containing mutations were mixed with other PCR fragments to cover the full eGFP coding sequence. This mixture served as a template for chimeric PCR using the primer pair of P10/P11. The full length mutant eGFP PCR fragments were digested with AvrII and cloned into the NheI site of pHypermut2. The mutant eGFPs in pHypermut2 were confirmed by sequencing.

EXAMPLE 2

Targeted Integration of the eGFP Gene into the Rearranged Ig Light Chain Locus and Evidence for Hypermutation of the eGFP Transgene The eGFP coding sequence was inserted into the pHypermut1 vector and transfected into the DT40 variant, $AID^{R1}CL1$, which conditionally expresses AID as a cDNA expression cassette after deletion of the endogenous AID genes (Arakawa et al., 2002). Clones which had integrated the construct into the rearranged Ig light chain locus were identified by PCR. Transcription of the eGFP gene in these clones is supposed to be driven by the Ig light chain promoter and terminated by the SV40 polyA signal (FIG. 1A). The clones contained two floxed transgenes, the bsr marker gene co-inserted in the rearranged Ig light chain locus and the AID-IRES-gpt gene of the $AID^{R1}$ progenitor clone. To remove the bsr marker alone or together with the AID expression cassette, Cre recombinase was induced by tamoxifen before subcloning by limited dilution (Arakawa et al., 2002). In this way, AID positive ($AID^{R1}IgL^{eGFP1}$) and negative ($AID^{-/-}IgL^{eGFP1}$) clones could be isolated which had deleted the bsr marker gene from the light chain locus.

The $AID^{R1}IgL^{eGFP1}$ and $AID^{-/-}IgL^{eGFP1}$ clones were subcloned by limited dilution, and 24 subclones of each clone

```
Primers.
P1      GGGACTAGTAAAATGATGCATAACCTTTTGCACA          (SEQ ID NO: 11)

P2      CGATTGAAGAACTCATTCCACTCAAATATACCC           (SEQ ID NO: 12)

P3      CCCACCGACTCTAGAGGATCATAATCAGCC              (SEQ ID NO: 13)

P4      TACAAAAACCTCCTGCCAGTGCAAGGAGCAGCTGATGGTT    (SEQ ID NO: 14)
        TTTACTGTCT

P5      GGGGGATCCAGATCTGTGACCGGTGCAAGTGATAGAAACT    (SEQ ID NO: 15)

P6      GGGAAGCTTTGGGAAATACTGGTGATAGGTGGAT          (SEQ ID NO: 16)

P7      GGGTCTAGACCTCTCAGCTTTTTCAGCAGAATAACCTCC     (SEQ ID NO: 17)

P8      GGTATAAAAGGGCATCGAGGTCCCCGGCAC              (SEQ ID NO: 18)

P9      AGTTCGAGGGCGACACCCTGGTGAACCGCA              (SEQ ID NO: 19)

P10     GAACCTAGGGCCACCATGGTGAGCAAGGGCGAGGA         (SEQ ID NO: 20)

P11     GAACCTAGGACTTGTACAGCTCGTCCATGCCG            (SEQ ID NO: 21)

P12     CCTAGCTCGATACAATAAACGCCATTTGAC              (SEQ ID NO: 22)

P13     TGGCTTCGGTCGGAGCCATGGAGATC                  (SEQ ID NO: 23)
```

Figure 1B:
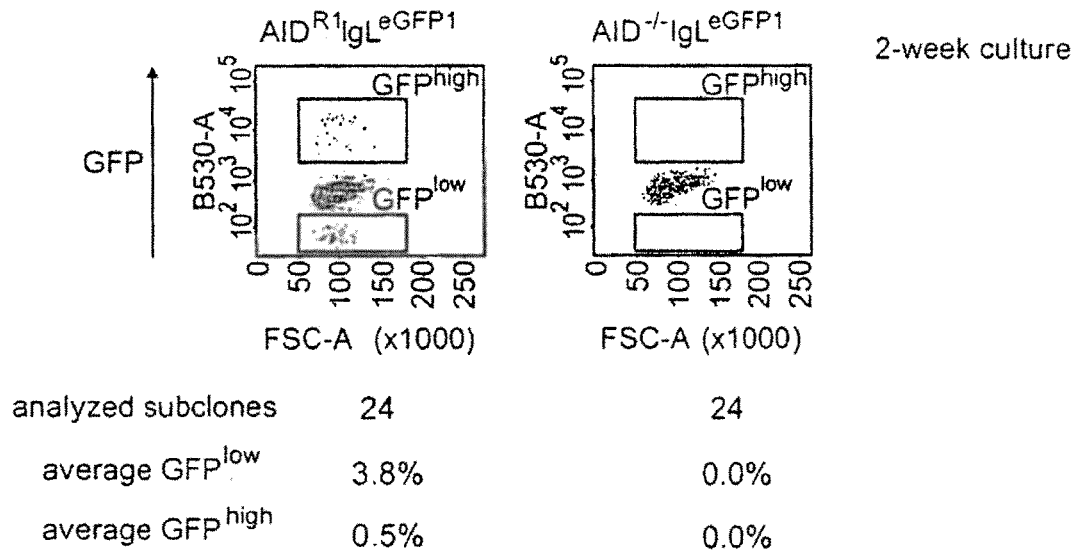

Color spectrum. Excitation and emission spectra were analyzed by the luminescence spectrometer LS50B (Perkin Elmer). One million cells were washed once with PBS, resuspended in 2 ml of PBS, and used for spectrum analysis. The relative ability to excite by lasers of different wavelengths was measured at fixed emission of 540 nm wavelength. The relative emission intensities at different wavelengths were measured after fixed excitation at 460 nm wavelength.

were analyzed by FACS for GFP brightness 14 days after subcloning. Subclones of the $AID^{R1}IgL^{eGFP1}$ clone contained cell populations showing lower and higher fluorescence than the dominant GFP positive cell population, whereas subclones of the $AID^{-/-}IgL^{eGFP1}$ clone consisted only of a homogeneous GFP positive population (FIG. 1B). This suggests that the eGFP gene inserted into the rearranged Ig light chain locus is diversified in $AID^{R1}IgL^{eGFP1}$ cells giving rise to variants of increased and decreased fluorescent intensity.

EXAMPLE 3:

Mutation Activity of Artificial Evolution System

Figure 2A:
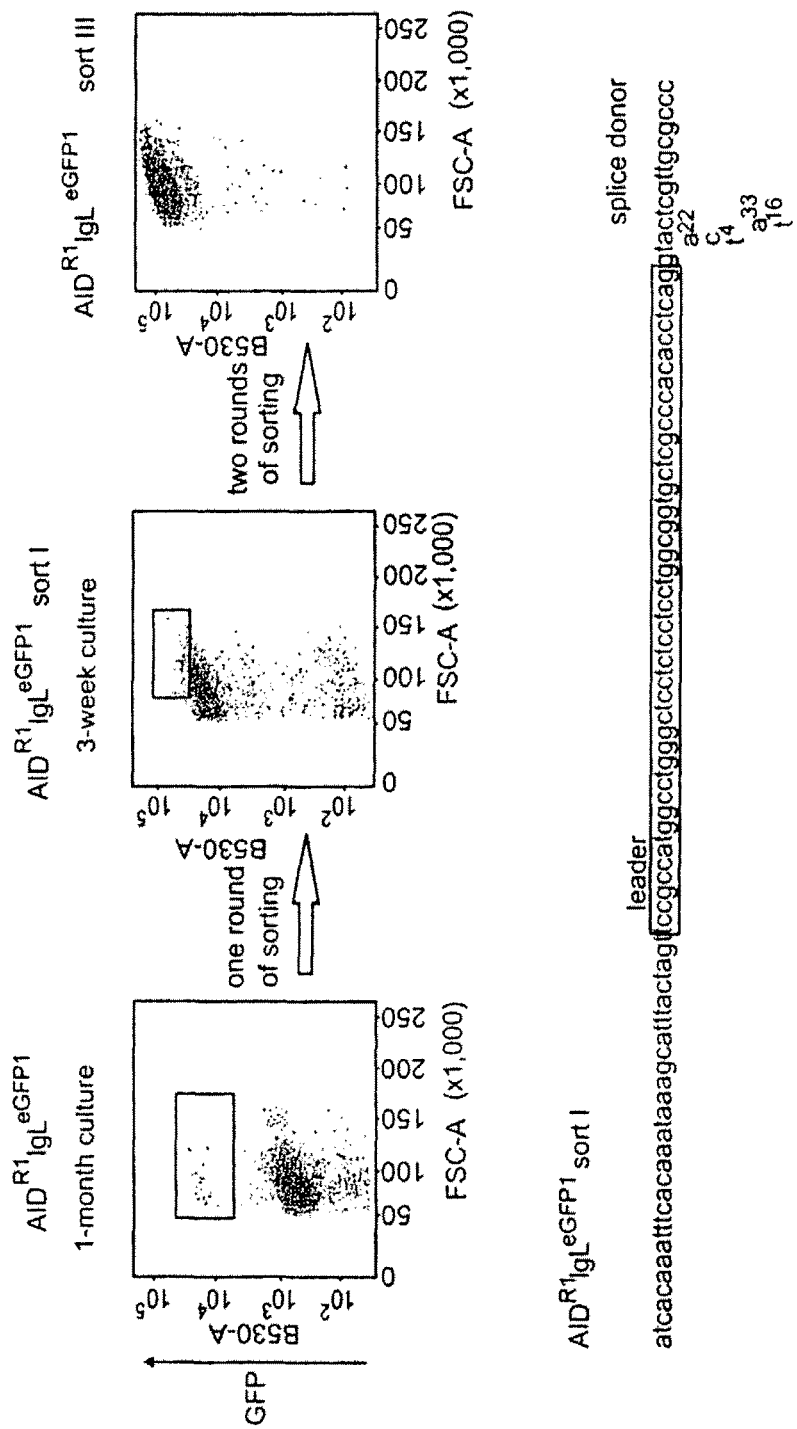

To analyze the mutation spectrum of the eGFP transgenes, the coding sequence was amplified by PCR from $AID^{R1}$ $IgL^{eGFP1}$ and $AID^{-/-}IgL^{eGFP1}$ cells 6 weeks after subcloning, cloned into a plasmid vector and sequenced. A total of 13 nucleotide changes were found within the 0.7 kb eGFP coding region of 39 sequences from the $AID_{R1}$ $IgL^{eGFP1}$ clone (Table 1). Assuming a DT40 doubling time of 10 h, the mutation rate of the eGFP coding region in the rearranged Ig light chain locus of $AID^{R1}IgL^{eGFP1}$ cells is about $4.7 \times 10^{-6}$ mutations per base pair and division. This mutation frequency is approximately three times lower than the mutation rate of the rearranged VJ segment in the pseudogene deleted $\Psi V^- AID^R$ cell line (Arakawa et al., 2004). In both cases the majority of mutations occurred at C/G base pairs (Table 1). Only 1 nucleotide change which possibly represents a PCR artifact was found in 26 sequences of the $AID^{-/-}IgL^{eGFP1}$ clone confirming that the mutation activity of the eGFP transgene is dependent on AID.

region downstream of the eGFP coding sequence by primer walking. This analysis revealed frequent mutations at the splice donor site of the Ig light chain leader intron (88 mutations/95 seq) (FIG. 2A, Table 1). Although the role of these mutations downstream of the eGFP polyA signal remains speculative, it is possible that they enhance fluorescence by increasing eGFP mRNA stability.

Figure 2C:
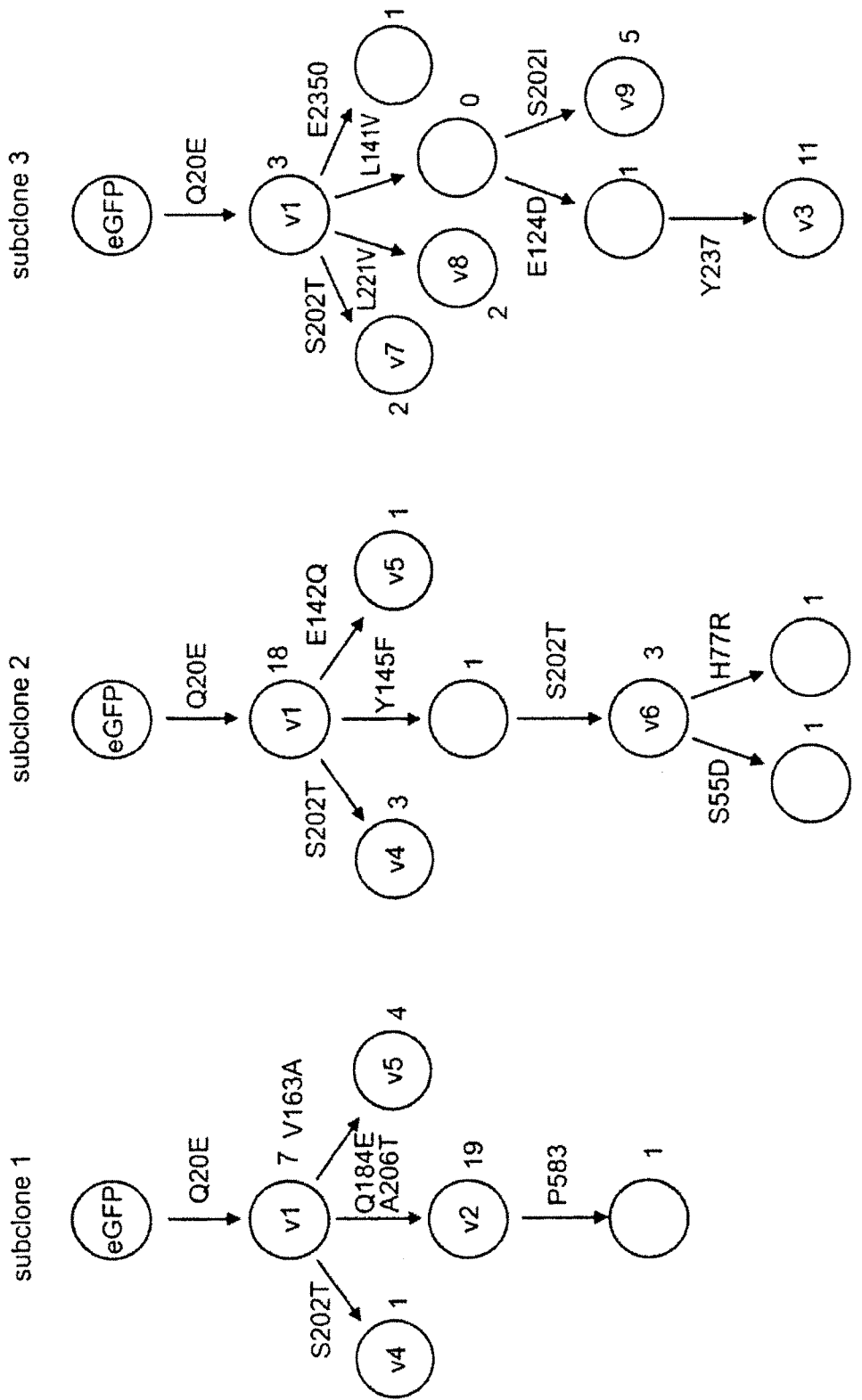

In contrast, most of the sequences after the third sort showed mutations in the eGFP coding sequence (221 mutations/85 seq) (FIG. 2B, Table 1). Comparison of the sequences of each sorted subclone allowed us to reconstruct evolutionary trees showing the stepwise accumulation of eGFP codon changes (FIG. 2C). Most of the codon changes were not shared by different subclones and their functional significance remains uncertain. However, a number of codon changes occurred independently in different subclones suggesting that they are related to the increased fluorescence of the sorted cells. Mutated eGFP sequences which were found more than once were named GFP variants (GFPv1-9).

TABLE 1

Mutation profile

| cell source | | gene | mutations | number of sequences | mutations/ sequence | mutations at C | G | A | T | duplication | deletion |
|---|---|---|---|---|---|---|---|---|---|---|---|
| $AID^{-/-}IgL^{eGFP1}$ | 6-week culture | eGFP (723 bp) | 1 | 26 | 0.04 | 0 | 0 | 1 | 0 | 0 | 0 |
| $AID^{R1}IgL^{eGFP1}$ | 6-week culture | eGFP (723 bp) | 13 | 39 | 0.33 | 5 | 8 | 0 | 0 | 1 | 0 |
| $AID^{R1}IgL^{eGFP1}$ | sort I | eGFP (723 bp)[1] | 15 | 95 | 0.16 | 8 | 6 | 1 | 0 | 0 | 0 |
| $AID^{R1}IgL^{eGFP1}$ | sort I | polyA-L (300 bp)[1] | 88 | 95 | 0.93 | 1 | 87 | 0 | 0 | 0 | 0 |
| $AID^{R1}IgL^{eGFP1}$ | sort III | eGFP (723 bp) | 221 | 85 | 2.60 | ## | 93 | 6 | 4 | 0 | 0 |

[1]Their sequences were derived from the different region of the same plasmids.

EXAMPLE 4

Sorting and Sequence Analysis of Cells Displaying Increased Fluorescence

The FACS analysis suggested that a few cells within the $AID^{R1}IgL^{eGFP1}$ culture accumulate mutations which increase either the abundance or the fluorescent intensity of the eGFP protein. To enrich these cells, ten million $AID^{R1}IgL^{eGFP1}$ cells were sorted by preparative FACS using a gate which included only the 0.05% brightest cells (FIG. 1C). The cells collected by the FACS sort were expanded and cycles of preparative cell sorting and expansion were repeated twice. Three consecutive sorts were performed independently for three $AID^{R1}IgL^{eGFP1}$ subclones. To trace the rise of mutations responsible for the increased fluorescence, the coding sequences of the eGFP genes were amplified by PCR from cells after the first and the third sort, cloned into a plasmid vector and sequenced. Unexpectedly, only few mutations and no obvious mutation signatures were found in the eGFP coding sequence after the first sort (Table 1) despite the fact that the sorted cells displayed increased fluorescence (FIG. 1C). We therefore extended the sequence analysis to the

EXAMPLE 5

Development of a New Vector for Transgene Evolution in DT40

Although it was possible to use pHypermut1 for the enhancement of eGFP, this vector is not ideally suited for transgene evolution in DT40, as mutations outside the transgene coding region had apparently been selected after the first sort. Therefore, a new targeting vector named pHypermut2 was developed in which the expression of the transgene should not be influenced by mutations of the rearranged Ig light chain gene, because transgene transcription is driven by the Rous sarcoma virus (RSV) promoter in the opposite direction of the light chain gene (FIG. 3A). pHypermut2 allows transgenes to be cloned into multiple cloning sites (NheI, EcoRV and BglII sites). The vector's puromycin resistance (puroR) cassette, located downstream of the transgene can be excised by Cre recombinase (Arakawa et al., 2001), but it is unlikely to interfere with transgene transcription or mutagenesis. A convenient feature of pHypermut2 is the presence of a SpeI site upstream of the RSV promoter which can be used for the insertion of gene conversion donor sequences (Kanayama et al., 2006).

Figure 3B:
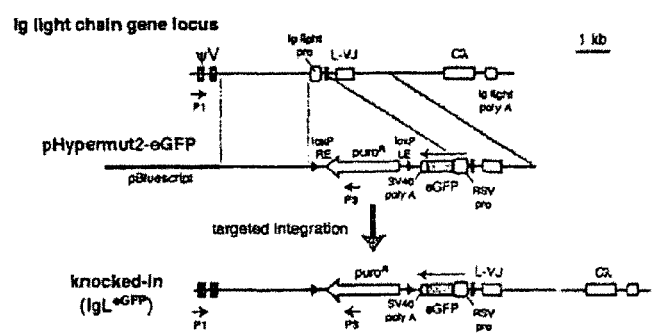
Figure 3C:
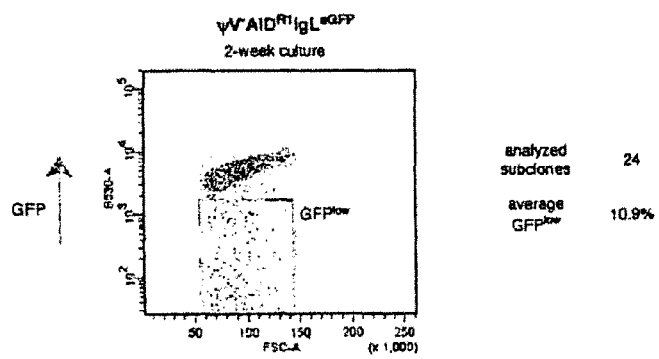

The eGFP transgene was inserted into pHypermut2, and the construct was transfected into the $\Psi V^- AID^{R1}$ cell line (Arakawa et al., 2004) (FIG. 3B). One of the stable transfected clones, ΨV⁻AID^{R1}IgL^{eGFP}, having integrated the construct into the rearranged Ig light chain locus was subcloned by limited dilution. FACS analysis of 24 subclones after 14 days of culture revealed that on average 10.9% of the cells showed decreased or lost fluorescence (FIG. 3C). This result indicates that transgenes inserted by pHypermut2 into the rearranged Ig light chain locus will be efficiently diversified by hypermutation.

EXAMPLE 6

Confirmation of the Variant GFP Phenotypes

The pHypermut2 vector can also be used to confirm the phenotypes of mutations by transfection of AID negative cells, because transgenes inserted by the vector in the light chain locus will be stably expressed as single copies. For this reason, all isolated GFP variants as well as the eGFP and the Emerald (Cubitt et al., 1999) control sequence were cloned into pHypermut2 and then transfected into the AID negative clone AID^{−/−}. Over half of all stable transfectants had integrated the constructs into the light chain locus and these clones were named according to the inserted transgene (AID^{−/−}IgL^{eGFP}, AID^{−/−}IgL^{Emerald}, AID^{−/−}IgL^{GFPv1}, etc.).

Figure 4A:
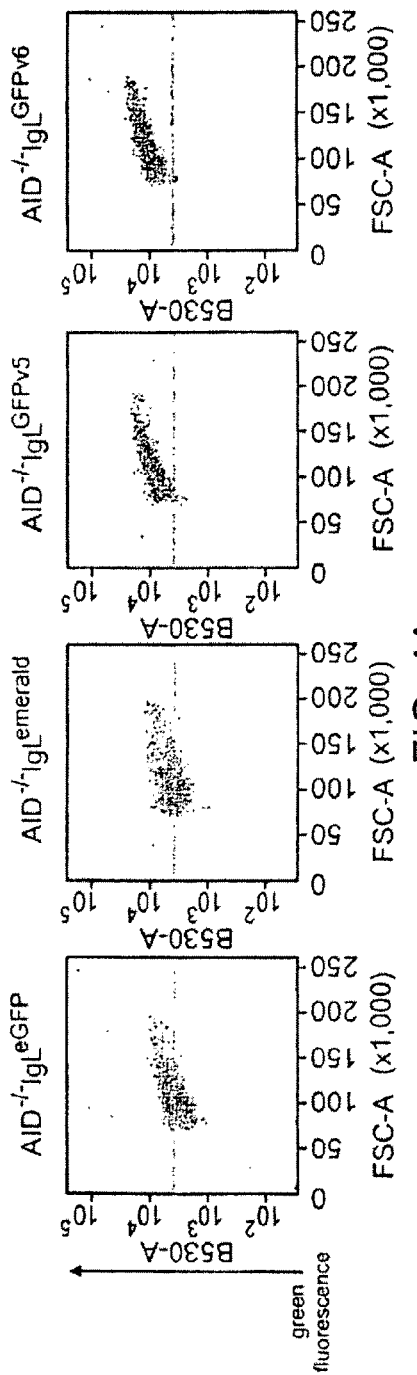
Figure 4B:
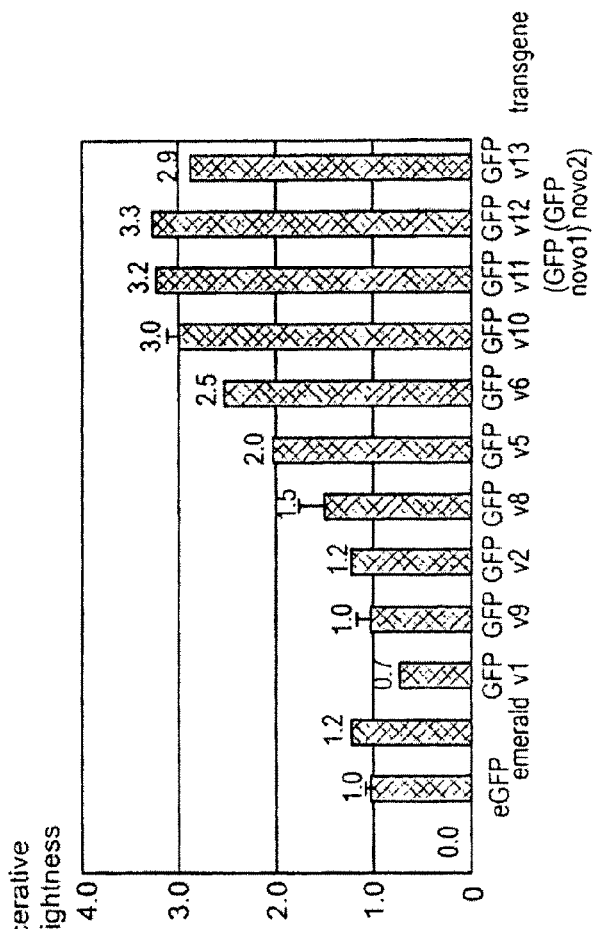

The fluorescent brightness of the different transfectants was compared by FACS (FIG. 4A). Two independent transfectants of each variant GFP gene were included in the experiment to account for variation among transfectants of the same gene (Table 2). This analysis revealed that the Emerald transfectant was 1.2 times brighter than the eGFP transfectant, four of the nine GFP variant transfectants (AID^{−/−}IgL^{GFPv2}, AID^{−/−}IgL^{GFPv5}, AID^{−/−}IgL^{GFPv6} and AID^{−/−}IgL^{GFPv8}) were brighter than the eGFP transfectant, and three GFP variant transfectants (AID^{−/−}IgL^{GFPv5}, AID^{−/−}IgL^{GFPv6} and AID^{−/−}IgL^{GFPv8}) were even brighter than the Emerald transfectant. In addition, little fluorescent variation was observed among transfectants of the same transgene (Table 2).

Among the transfectants of GFP variants, AID^{−/−}IgL^{GFPv6} was the brightest (2.5-fold more than the AID^{−/−}IgL^{eGFP}) and AID^{−/−}IgL^{GFPv5} was the second brightest (2.0-fold brighter than the AID^{−/−}IgL^{eGFP}) (FIG. 4A, Table 2). In order to compare the brightness of eGFP and GFPv6 in human cells, the pHypermut2 constructs of GFPv6 and eGFP were transiently transfected into the human embryonic kidney cell line, HEK293T. Cells transfected by the GFPv6 construct showed clearly more fluorescence by FACS analysis than cells transfected by the eGFP construct (data not shown).

TABLE 2

Amino acid changes and brightness of GFP variants

| GFP variant | amino acid changes | number of sequences | subclone | relative brightness |
|---|---|---|---|---|
| | change from wild-type GFP | | | |
| eGFP | 1aV, F64L, S65T, H231L, 239S | — | — | 1.0 ± 0.1 |
| | change from eGFP | | | |
| GFPv1 | Q80E | 28 | 1, 2, 3 | 0.7 ± 0.0 |
| GFPv2 | Q80E, Q184E, A206T | 19 | 1 | 1.2 ± 0.0 |
| GFPv3 | Q80E, E124D, L141V, Y237stop | 11 | 3 | 0.3 ± 0.0 |
| GFPv4 | Q80E, S202T | 4 | 1, 2 | 0.9 ± 0.1 |
| GFPv5 | Q80E, V163A | 4 | 1 | 2.0 ± 0.0 |
| GFPv6 | Q80E, Y145F, S202T | 3 | 2 | 2.5 ± 0.0 |
| GFPv7 | Q80E, S208T | 2 | 3 | 0.7 ± 0.1 |
| GFPv8 | Q80E, L221V | 2 | 3 | 1.5 ± 0.3 |
| GFPv9 | Q80E, L141V, S202I | 5 | 3 | 1.0 ± 0.1 |
| GFPv10 | Q80E, Y145F, V163A, S202T | — | — | 3.0 ± 0.1 |
| GFPv11 (GFPnovo1) | Y145F, V163A, S202T | — | — | 3.2 ± 0.0 |
| GFPv12 (GFPnovo2) | Y145F, V163A, S202T, L221V | — | — | 3.3 ± 0.0 |
| GFPv13 | L141V, Y145F, V163A, Q184E, S202T, A206T, L221V | — | — | 2.9 ± 0.1 |
| | change from wild-type GFP | | | |
| emerald | S65T, S72A, N149K, M153T, I167T | — | — | 1.2 |

EXAMPLE 7

Increased Fluorescence by the Combination of Mutations

Since a number of codon changes were not shared among GFP variants, we wondered whether combinations of these mutations in a single sequence would further intensify fluorescence. At first, Y145F and S202T of GFPv6 were combined with V163A of GFPv5 to produce GFPv10. Because GFPv1 harboring the single Q80E mutation showed less brightness than eGFP, Q80E was subtracted from GFPv10 to generate GFPv11. L221V of GFPv8 was also added to GFPv11, thereby generating GFPv12. Finally Q184E and A206T of GFPv2 as well as L141V of GFPv9 were added to GFPv12 to generate GFPv13. These new GFP variants were cloned into pHypermut2, and inserted into the rearranged Ig light chain locus of AID^{−/−}.

When the transfectants of the new GFP variant were analyzed by FACS (FIG. 4B, Table 2), all showed more brightness than AID^{−/−}IgL^{GFPv6}. AID^{−/−}IgL^{GFPv10} was 3.0-fold brighter than AID^{−/−}IgL^{eGFP}, but AID^{−/−}IgL^{GFPv11} and AID$^{-/-}$IgL$^{GFPv12}$ were even brighter, displaying 3.2- and 3.3-fold more fluorescence respectively than AID$^{-/-}$IgL$^{eGFP}$. AID$^{-/-}$IgL$^{GFPv13}$ did not surpass the brightness of the other variant GFP transfectants. The novel GFP variants GFPv11 and GFPv12 which offer the most potential for the labeling of vertebrate cells were named GFPnovo1 and GFPnovo2, respectively.

EXAMPLE 8

Spectral Properties of the New GFP Variants

Figure 4C:
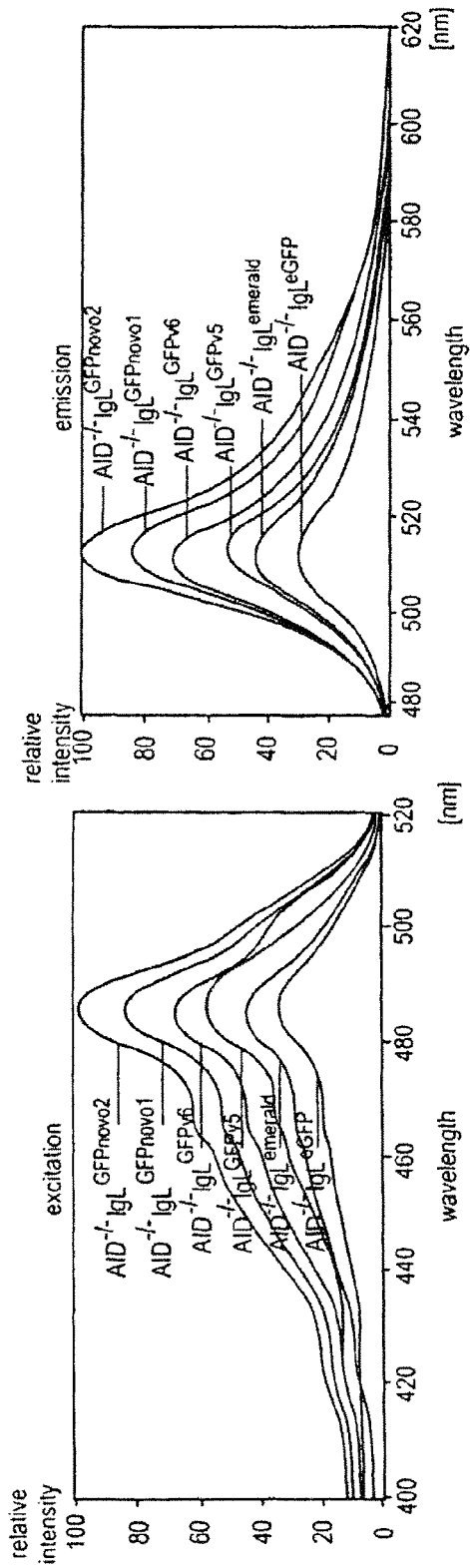

The excitation and emission maxima of eGFP are at 488 nm and 509 nm wavelength respectively (Patterson et al., 1997; Cubitt et al., 1999). To determine the spectral profiles of the new variant GFP proteins, the control and variant gene transfectants (AID$^{-/-}$IgL$^{eGFP}$, AID$^{-/-}$IgL$^{Emerald}$, AID$^{-/-}$IgL$^{GFPv5}$, AID$^{-/-}$IgL$^{GFPv6}$, AID$^{-/-}$IgL$^{GFPnovo1}$ and the AID$^{-/-}$IgL$^{GFPnovo2}$) were analyzed using a luminescence spectrometer (FIG. 4C). This analysis showed that only the fluorescent intensity, but not the excitation and emission spectra have been changed in the variant GFP transfectants.

Figure 4D:
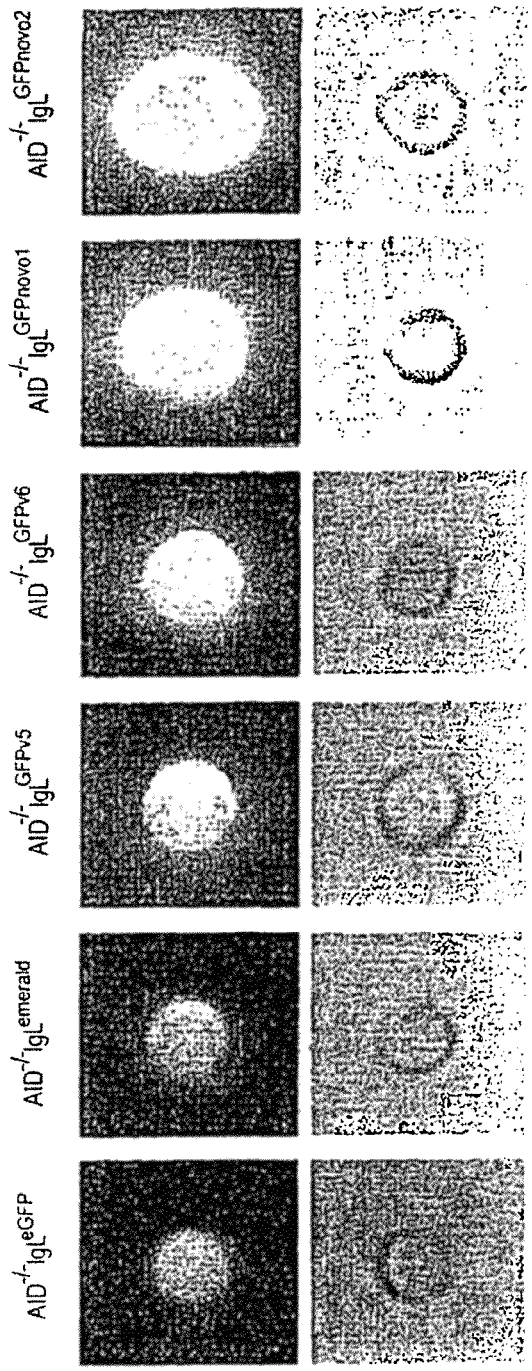

We also examined cells of the eGFP, Emerald and variant GFP transfectants by fluorescence microscopy (FIG. 4D). Consistent with the FACS and spectrometer analysis, cells of the GFPv5, GFPv6, GFPnovo1 and GFPnovo2 transfectants produced brighter images than cells of the eGFP and Emerald transfectants, but there was no noticeable change of color.

References

Anderson, M. T., Tjioe, I. M., Lorincz, M. C., Parks, D. R., Herzenberg, L. A., Nolan, G. P., and Herzenberg, L. A. (1996). Simultaneous fluorescence-activated cell sorter analysis of two distinct transcriptional elements within a single cell using engineered green fluorescent proteins. Proc Natl Acad Sci USA 93(16), 8508-8511.

Arakawa, H., Saribasak, H. and Buerstedde, J-M. (2004) Activation-induced cytidine deaminase initiates immunoglobulin gene conversion and hypermutation by a common intermediate. PLoS Biol. 2, E179.

Arakawa, H., Hauschild, J. and Buerstedde, J. M. (2002) Requirement of the activation-induced deaminase (AID) gene for immunoglobulin gene conversion. Science, 295, 1301-1306.

Arakawa, H., Lodygin, D. and Buerstedde, J. M. (2001) Mutant loxP vectors for selectable marker recycle and conditional knock-outs. BMC Biotechnology, 1, 7.

Chalfie, M., Tu, Y., Euskirchen, G., Ward, W. W., and Prasher, D. C. (1994). Green fluorescent protein as a marker for gene expression. Science 263, 802-805.

Cheng, L. Z., Fu, J., Tsukamoto, A. and Hawley, R. G. (1996). Use of green fluorescent protein variants to monitor gene transfer and expression in mammalian cells. Nat. Biotechnol. 14, 606-9

Cormack, B., P., Valdivia, R. H. and Falkow, S. (1996). FACS-optimized mutants of the green fluorescent protein (GFP). Gene 173, 33-38.

Crameri, A., Whitehorn, E. A., Tate, E. and Stemmer, W. P. (1996) Improved green fluorescent protein by molecular evolution using DNA shuffling. Nat. Biotechnol. 14, 315-319.

Cubitt, A. B., Woollenweber, L. A. and Heim, R. (1999) Understanding structure-function relationships in the Aequorea victoria green fluorescent protein. Methods Cell Biol., 58, 19-30.

Delagrave S., Hawtin R. E., Silva C. M., Yang M. M. and Youvan D. C. (1995). Red-shifted excitation mutants of the green fluorescent protein. Biotechnology 13, 151-14.

Heim, R. (1995). Green fluorescent protein forms for energy transfer. Methods Enzymol. 302, 408-423.

Heim, R. and Tsien, R. Y. (1996). Engineering green fluorescent protein for improved brightness, longer wavelengths and fluorescence resonance energy transfer. Current Biology 6, 178-182

Kanayama, N., Todo, K., Takahashi, S., Magari, M. and Ohmori, H. (2006) Genetic manipulation of an exogenous non-immunoglobulin protein by gene conversion machinery in a chicken B cell line. Nucleic Acids Res. 34, e10.

Nagai, T., Ibata, K., Park, E. S., Kubota, M., Mikoshiba, K. and Miyawaki, A. (2002) A variant of yellow fluorescent protein with fast and efficient maturation for cell-biological applications. Nat. Biotechnol. 20, 87-90.

Ormo, M., Cubitt, A. B., Kallio, K., Gross, L. A., Tsien, R. Y. and Remington, S. J. (1996) Crystal structure of the Aequorea victoria green fluorescent protein. Science 273, 1392-1395.

Patterson, G. H., Knobel, S. M., Sharif, W. D., Kain, S. R. and Piston, D. W. (1997) Use of the green fluorescent protein and its mutants in quantitative fluorescence microscopy. Biophys. J. 73, 2782-2790.

Prasher, D. C., Eckenrode, V. K., Ward, W. W., Prendergast, F. G., and Cormier, M. J. (1992). Primary structure of the Aequora Victoria green-fluorescent protein. Gene 111, 229-233.

Rekas, A., Alattia, J. R., Nagai, T., Miyawaki, A. and Ikura, M. (2002) Crystal structure of venus, a yellow fluorescent protein with improved maturation and reduced environmental sensitivity. J. Biol. Chem. 277, 50573-50578.

Siemering, K. R., Golbik, R., Sever, R., and Haseloff, J. (1996). Mutations that suppress the thermosensitivity of green fluorescent protein. Curr. Biol. 6, 1653-1663.

Tsien (1998). The Green Fluorescent Protein. Annu. Rev. Biochem. 67, 509-544.

Yang, T. T., Sinai, P., Green, G., Kitts, P. A., Chen, Y. T., Lybarger, L., Chervenak, R., Patterson, G. H., Piston and D. W., Kain, S. R. (1998). Improved fluorescence and dual color detection with enhanced blue and green variants of the green fluorescent protein. J Biol Chem. 273, 8212-8216.

Zacharias, D. A. (2002). Sticky caveats in an otherwise glowing report: oligomerizing fluorescent proteins and their use in cell biology. Sci STKE 131, PE23.

Zacharias, D. A. and Tsien, R. Y. (2006) Molecular biology and mutation of green fluorescent protein. Methods Biochem. Anal., 47, 83-120.

Zapata-Hommer, O. and Griesbeck, O. (2003) Efficiently folding and circularly permuted variants of the Sapphire mutant of GFP. BMC Biotechnol. 3, 5.

Zeller, R. W., Weldon, D. S., Pellatiro, M., A. and Cone, A. C. (2006). Optimized Green Fluorescent Protein Variants Provide Improved Single Cell Resolution of Transgene Expression in Ascidian Embryos; Developmental Dynamics 235, 456-467.

The invention claimed is:

1. An isolated or purified nucleic acid molecule encoding a polypeptide having a fluorescence emission activity with a maximum emission at 505 to 515 nm, wherein said nucleic acid molecule is selected from the group consisting of
    (a) a nucleic acid encoding a polypeptide SEQ ID NO: 2;
    (b) a nucleic acid having the DNA sequence of SEQ ID NO: 1; and
    (c) a nucleic acid that hybridizes under stringent conditions to the complementary strand of
        the nucleic acid of (a), and wherein said nucleic acid of
        (c) encodes a polypeptide having a phenylalanine at position 146 of SEQ ID NO:2 and a threonine at position 203 of SEQ NO:2; and
    (d) a nucleic acid that hybridizes under stringent conditions to the complementary strand of the nucleic acid of (b), and wherein said nucleic acid of (d) has at positions 438 to 440 of SEQ ID NO: 1 a nucleotide triplet selected from the group consisting of TTT and TTC; and at positions 609 to 611 of SEQ ID NO: 1 a nucleotide triplet selected from the group consisting of ACT, ACC, ACA, ACG; and
    wherein the nucleic acid molecule encodes a polypeptide that has a fluorescence emission activity with a maximum emission at 505 to 515 nm and has a fluorescence enhanced by at least the factor of 2.5as compared to the polypeptide having the amino acid sequence of SEQ ID NO: 10.

2. The isolated or purified nucleic acid molecule of claim 1, wherein in the nucleic acid molecule encoding a polypeptide having the amino acid sequence of SEQ ID NO: 2 alanine replaces valine at position 164.

3. The isolated or purified nucleic acid molecule of claim 1 or 2, wherein in the nucleic acid molecule encoding a polypeptide having the amino acid sequence of SEQ ID NO: 2 valine replaces leucine at position 222.

4. The isolated or purified nucleic acid molecule of claim 1 or 2, which is DNA.

5. A vector comprising the isolated or purified nucleic acid molecule of claim 1.

6. The isolated or purified nucleic acid molecule of claim 1, the nucleic acid molecule encoding a fusion polypeptide.

7. The isolated or purified nucleic acid molecule of claim 6, wherein the fusion polypeptide comprises a His-tag, a Strep-tag, a GST-tag, a TAP tag, biotin, an HA tag or a signal sequence for intra- or extracellular targeting comprising nuclear localisation signals, signal to retain a protein in the endoplasmatic reticulum, to target a protein to peroxisomes, or a secretion signal or signal for trans-Golgi-network sorting.

8. A diagnostic composition comprising at least one of
    (a) the isolated or purified nucleic acid molecule of claim 1 or 2, or
    (b) the vector of claim 5.

9. A method of detecting the expression of a gene of interest, comprising
    (a) operably linking the nucleic acid molecule of any one of claims 1 to 4 with a promoter controlling said gene of interest or
    (a)' fusing the nucleic acid molecule of any one of claims 1 to 4 to said gene of interest and
    (b) detecting the fluorescence of the protein encoded by said nucleic acid molecule.

10. A method of detecting the activity of a promoter of interest, comprising operably linking the nucleic acid molecule of any one of claims 1 to 4 with said promoter of interest and detecting the fluorescence of the protein encoded by said nucleic acid molecule.

11. A kit comprising at least one of
    (a) the isolated or purified nucleic acid molecule of claim 1 or 2; or
    (b) the vector of claim 5.

* * * * *

SEQUENCE LISTING

<160> NUMBER OF SEQ ID NOS: 26

<210> SEQ ID NO 1
<211> LENGTH: 723
<212> TYPE: DNA
<213> ORGANISM: Aequorea Victoria

<400> SEQUENCE: 1

```
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctagaat acaacttcaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgacca cccagtccgc cctgagcaaa gaccccaacg agaagcgcga tcacatggtc     660
ctgctggagt tcgtgaccgc cgccgggatc actctcggca tggacgagct gtacaagtcc     720
tag                                                                   723
```

<210> SEQ ID NO 2
<211> LENGTH: 240
<212> TYPE: PRT
<213> ORGANISM: Aequorea Victoria

<400> SEQUENCE: 2

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Phe Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
```

-continued

```
                    180                 185                 190
Pro Val Leu Leu Pro Asp Asn His Tyr Leu Thr Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys Ser
225                 230                 235                 240

<210> SEQ ID NO 3
<211> LENGTH: 723
<212> TYPE: DNA
<213> ORGANISM: Aequorea Victoria

<400> SEQUENCE: 3
atggtgagca agggcgagga gctgttcacc ggggtggtgc ccatcctggt cgagctggac     60
ggcgacgtaa acggccacaa gttcagcgtg tccggcgagg gcgagggcga tgccacctac    120
ggcaagctga ccctgaagtt catctgcacc accggcaagc tgcccgtgcc ctggcccacc    180
ctcgtgacca ccctgaccta cggcgtgcag tgcttcagcc gctaccccga ccacatgaag    240
cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctgggcac    420 aagctagaat acaacttcaa cagccacaac gtctatatca tggccgacaa gcagaagaac    480
ggcatcaagg cgaacttcaa gatccgccac aacatcgagg acggcagcgt gcagctcgcc    540
gaccactacc agcagaacac ccccatcggc gacggccccg tgctgctgcc cgacaaccac    600
tacctgacca cccagtccgc cctgagcaaa gaccccaacg agaagcgcga tcacatggtc    660
ctgctggagt tcgtgaccgc cgccgggatc actctcggca tggacgagct gtacaagtcc    720
tag                                                                  723

<210> SEQ ID NO 4
<211> LENGTH: 240
<212> TYPE: PRT
<213> ORGANISM: Aequorea Victoria

<400> SEQUENCE: 4

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140
```

```
Asn Phe Asn Ser His Asn Val Tyr Ile Met Ala Asp Lys Gln Lys Asn
145                 150                 155                 160

Gly Ile Lys Ala Asn Phe Lys Ile Arg His Asn Ile Glu Asp Gly Ser
            165                 170                 175

Val Gln Leu Ala Asp His Tyr Gln Gln Asn Thr Pro Ile Gly Asp Gly
        180                 185                 190

Pro Val Leu Leu Pro Asp Asn His Tyr Leu Thr Thr Gln Ser Ala Leu
    195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys Ser
225                 230                 235                 240

<210> SEQ ID NO 5
<211> LENGTH: 723
<212> TYPE: DNA
<213> ORGANISM: Aequorea Victoria

<400> SEQUENCE: 5
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctagaat acaacttcaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgacca cccagtccgc cctgagcaaa gaccccaacg agaagcgcga tcacatggtc     660
ctggtggagt tcgtgaccgc cgccgggatc actctcggca tggacgagct gtacaagtcc     720
tag                                                                   723

<210> SEQ ID NO 6
<211> LENGTH: 240
<212> TYPE: PRT
<213> ORGANISM: Aequorea Victoria

<400> SEQUENCE: 6

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110
```

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
            130                 135                 140

Asn Phe Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Thr Thr Gln Ser Ala Leu
        195                 200                 205

Ser Lys Asp Pro Asn Glu Lys Arg Asp His Met Val Leu Val Glu Phe
    210                 215                 220

Val Thr Ala Ala Gly Ile Thr Leu Gly Met Asp Glu Leu Tyr Lys Ser
225                 230                 235                 240

<210> SEQ ID NO 7
<211> LENGTH: 723
<212> TYPE: DNA
<213> ORGANISM: Aequorea Victoria

<400> SEQUENCE: 7
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctagaat acaacttcaa cagccacaac gtctatatca tggccgacaa gcagaagaac     480
ggcatcaagg cgaacttcaa gatccgccac aacatcgagg acggcagcgt gcagctcgcc     540
gaccactacc agcagaacac ccccatcggc gacggccccg tgctgctgcc cgacaaccac     600
tacctgacca cccagtccgc cctgagcaaa gaccccaacg agaagcgcga tcacatggtc     660
ctggtggagt tcgtgaccgc cgccgggatc actctcggca tggacgagct gtacaagtcc     720
tag                                                                   723

<210> SEQ ID NO 8
<211> LENGTH: 240
<212> TYPE: PRT
<213> ORGANISM: Aequorea Victoria

<400> SEQUENCE: 8

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys

```
                65                  70                  75                  80
Gln His Asp Phe Phe Lys Ser Ala Met Pro Glu Gly Tyr Val Gln Glu
                    85                  90                  95

Arg Thr Ile Phe Phe Lys Asp Asp Gly Asn Tyr Lys Thr Arg Ala Glu
                    100                 105                 110

Val Lys Phe Glu Gly Asp Thr Leu Val Asn Arg Ile Glu Leu Lys Gly
                    115                 120                 125

Ile Asp Phe Lys Glu Asp Gly Asn Ile Leu Gly His Lys Leu Glu Tyr
                    130                 135                 140

Asn Phe Asn Ser His Asn Val Tyr Ile Met Ala Asp Lys Gln Lys Asn
145                 150                 155                 160

Gly Ile Lys Ala Asn Phe Lys Ile Arg His Asn Ile Glu Asp Gly Ser
                    165                 170                 175

Val Gln Leu Ala Asp His Tyr Gln Gln Asn Thr Pro Ile Gly Asp Gly
                    180                 185                 190

Pro Val Leu Leu Pro Asp Asn His Tyr Leu Thr Thr Gln Ser Ala Leu
                    195                 200                 205

Ser Lys Asp Pro Asn Glu Lys Arg Asp His Met Val Leu Val Glu Phe
        210                 215                 220

Val Thr Ala Ala Gly Ile Thr Leu Gly Met Asp Glu Leu Tyr Lys Ser
225                 230                 235                 240

<210> SEQ ID NO 9
<211> LENGTH: 723
<212> TYPE: DNA
<213> ORGANISM: Aequorea Victoria

<400> SEQUENCE: 9
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctagaat acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
ctgctggagt tcgtgaccgc cgccgggatc actctcggca tggacgagct ctacaagtcc     720
tag                                                                   723

<210> SEQ ID NO 10
<211> LENGTH: 240
<212> TYPE: PRT
<213> ORGANISM: Aequorea Victoria

<400> SEQUENCE: 10

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
                    20                  25                  30
```

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
 50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
            130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
            195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys Ser
225                 230                 235                 240

<210> SEQ ID NO 11
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 11
gggactagta aaatgatgca taacctttg caca                                34

<210> SEQ ID NO 12
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 12
cgattgaaga actcattcca ctcaaatata ccc                                33

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 13
cccaccgact ctagaggatc ataatcagcc                                    30

<210> SEQ ID NO 14
<211> LENGTH: 50
<212> TYPE: DNA
<213> ORGANISM: Artificial Sequence -continued

```
<220> FEATURE:
<223> OTHER INFORMATION: Description of Artificial Sequence: Primer

<400> SEQUENCE: 14
tacaaaaacc tcctgccagt gcaaggagca gctgatggtt tttactgtct        50

<210> SEQ ID NO 15
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 15
gggggatcca gatctgtgac cggtgcaagt gatagaaact                   40

<210> SEQ ID NO 16
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 16
gggaagcttt gggaaatact ggtgataggt ggat                         34

<210> SEQ ID NO 17
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 17
gggtctagac ctctcagctt tttcagcaga ataacctcc                    39

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 18
ggtataaaag ggcatcgagg tccccggcac                              30

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 19
agttcgaggg cgacaccctg gtgaaccgca                              30

<210> SEQ ID NO 20
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 20
gaacctaggg ccaccatggt gagcaagggc gagga                        35
```

```
<210> SEQ ID NO 21
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 21
gaacctagga cttgtacagc tcgtccatgc cg                                   32

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 22
cctagctcga tacaataaac gccatttgac                                      30

<210> SEQ ID NO 23
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 23
tggcttcggt cggagccatg gagatc                                          26

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Signal
      sequence

<400> SEQUENCE: 24

Pro Pro Lys Lys Lys Arg Lys Val
1               5

<210> SEQ ID NO 25
<211> LENGTH: 4
<212> TYPE: PRT
<213> ORGANISM: Artificial Sequence
<220> FEATURE:
<223> OTHER INFORMATION: Description of Artificial Sequence: Signal
      sequence

<400> SEQUENCE: 25

Lys Asp Glu Leu
1

<210> SEQ ID NO 26
<211> LENGTH: 100
<212> TYPE: DNA
<213> ORGANISM: Aequorea victoria

<400> SEQUENCE: 26
atcacaaatt tcacaaataa agcatttact agttccgcca tggcctgggc tcctctcctc    60
ctggcggtgc tcgcccacac ctcaggtact cgttgcgccc                         100
```